United States Patent [19]

Leung et al.

[11] Patent Number: 5,955,645
[45] Date of Patent: Sep. 21, 1999

[54] THROMBIN RECEPTOR DEFICIENT TRANSGENIC MICE

[75] Inventors: Wai-Ping Leung, San Diego, Calif.; Patricia Andrade-Gordon, Doylestown, Pa.; Lubing Zhou, East Brunswick, N.J.

[73] Assignee: Ortho Pharmaceutical Corporation, Raritan, N.J.

[21] Appl. No.: 08/847,953

[22] Filed: Apr. 22, 1997

Related U.S. Application Data

[60] Provisional application No. 60/016,070, Apr. 23, 1996, and provisional application No. 60/020,544, Jun. 25, 1996.

[51] Int. Cl.$^6$ .............................. C12N 5/00; C12N 15/85; C12N 15/00; C12N 5/06
[52] U.S. Cl. ................................. 800/18; 800/21; 800/22; 435/325; 435/455; 435/463
[58] Field of Search ..................................... 800/2, 18, 21, 800/22; 435/325, 354, 320.1, 172.3, 455, 463; 536/23.5

[56] References Cited

PUBLICATIONS

Bradley, A. (1992) Modifying the mouse: Design and desire. Bio/Technology 10:534–539, 1992.

Campbell, K.H.S. and Wilmut, I. (1997) Totipotency and multipotentiality of cultured cells: Applications and progress. Theriogenology 47:63–72, 1997.

Evans, M.J. and Kaufman, M.H. (1981) Establishment in culture of pluripotential cells from mouse embryos. Nature 292:154–156, 1981.

Vu, T.–K.H. et al. (1991) Molecular cloning of a functional thrombin receptor reveals a novel proteolytic mechanism of receptor activation. Cell 64:1057–1068, 1991.

Zijlstra et al. (1989) Germ–line transmission of a disrupted B2–microglobulin gene produced by homologous recombination in embryonic stem cells. Nature 342:435–438.

*Primary Examiner*—Bruce R. Campell
*Assistant Examiner*—Anne-Marie Baker
*Attorney, Agent, or Firm*—John W. Wallen, III

[57] ABSTRACT

A transgenic animal with alterations in an thrombin receptor gene is prepared by introduction of an altered thrombin receptor gene into a host animal. The resulting transgenic animals do not produce functional thrombin receptor molecules.

6 Claims, 11 Drawing Sheets

FIG. 1A

```
  1  GGCAGCCTTG  GACAATGGGG  CCCCGGCGCT  TGCTGATCGT  CGCCCTCGGC
CTGAATTC---------------------------------------->MTR-5
 51  CTCAGCCTGT  GCGGTCCCTT  GCTGTCTTCC  CGGTCCCTA   TGAGCCAGCC
                           ---->MTR-1
101  AGAATCAGAG  AGGACAGATG  CTACGGTGAA  CCCCGCTCA   TTCTTTCTAA
151  GGAATCCCAG  TGAAAATACA  TTTGAACTGG  TCCCCTGGG   GGATGAGGAG
201  GAGGAGAGA   AAAATGAAAG  CGTCCTGCTG  GAGGGTAGGG  CAGTCTACTT
251  AAATATAAGC  CTCCCTCCTC  ACACGCCGCC  TCCTCCCTC   ATCTCCGAGG
301  ACGCCTCCGG  ATATCTGACC  AGCCCCTGGC  TGACGCTCTT  CATGCCCTCC
351  GTGTACACGA  TTGTGTTCAT  TGTCAGCCCT  CCTCTGAACG  TCCTGGCCAT
401  CGCAGTGTTC  GTCTTGAGGA  TGAAGGTCAA  GAAGCCGGCC  GTGGTGTACA
451  TGCTGCACCT  GGCCATGGCC  GACGTGCTCT  TCGTGTCGGT  GCTCCCTTCC
501  AAGATCAGCT  ACTACTTCTC  CGGCACTGAT  TGGCAGTTCG  GGTCTGGAAT
551  GTGCCGTTTC  GCCACCGCAG  CGTTTTACTA  TAACATGTAC  GCCTCCATCA
601  TGCTCATGAC  GGTCATAAGC  ATTGACCGGT  TCCTGGCGGT  GGTGTATCCG
     ---------T--------------------->MTR-3
```

FIG. 1B

```
651   ATCCAGTCCC  TGTCCTGGCG  CACTCTGGGC  GGAGCCAACT  TCACTTGCGT
701   GGTCATTTGG  GTGATGGCCA  TCATGGGGGT  GGTGCCCCTT  CTCCTCAAGG
751   AGCAGACCAC  CCGAGTTCCG  GGACTCAACA  TCACCACCTG  CCACGATCTC
801   CTCAGTGAGA  ACCTGATGCA  AGGCTTTTAC  TCGTACTACT  TCTCGGCCTT
851   CTCCGCCATC  TTCTTTCTTG  TGCCGTTGAT  CGTTTCCACG  GTCTGCTACA
901   CGTCCATCAT  CCGGTGCCTG  AGCTCCTCCG  CGGTTGCCAA  CCGGAGCAAG
951   AAGTCGCGGG  CTTTGTTCCT  GTCTGCCGCG  GTGTTCTGCA  TCTTCATCGT
1001  CTGCTTTGGG  CCCACCAACG  TCCTCCTGAT  TGTGCACTAC  CTTTTCCTCT
1051  CCGACAGTCC  TGGTACGGAG  GCAGCCTACT  TTGCTTACCT  CCTCTGCGTC
1101  TGTGTGACGA  GCGTGAGCTG  CTGCATCGAT  CCGTTGATTT  ACTACTACGC
1151  CTCCTCCGAG  TGCCAGAGGC  ACCTCTACAG  CATCTTGTGC  TGCAAAGAAA
1201  GCTCTGATCC  CAACAGTTGC  AACAGCACCG  GCCAGCTGAT  GCCGAGTAAA
1251  ATGGATACCT  GCTCTAGTCA  CCTGAATAAC  AGCATATACA  AAAAGCTATT
1301  AGCTTAGGGA  AA
      ‑‑‑‑‑‑‑TTCAG  MTR-2
                                                          ←‑‑‑‑
```

TR Knockout Mice

-/-   +/-   +/+

> 16 Kb 5.1 Kb

SpeI cut
TR SacI flanking probe

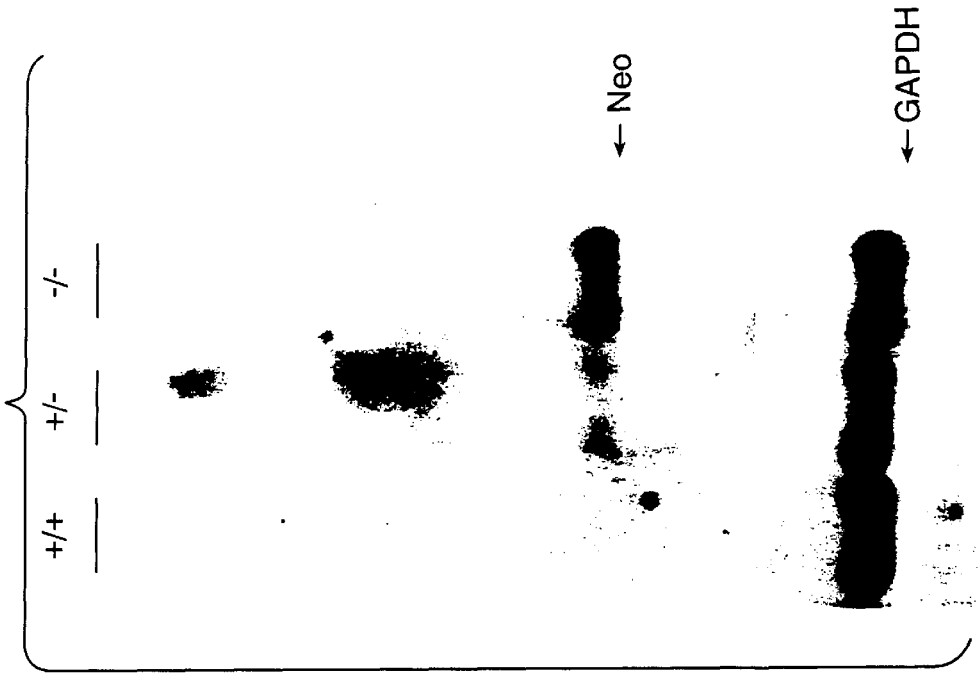
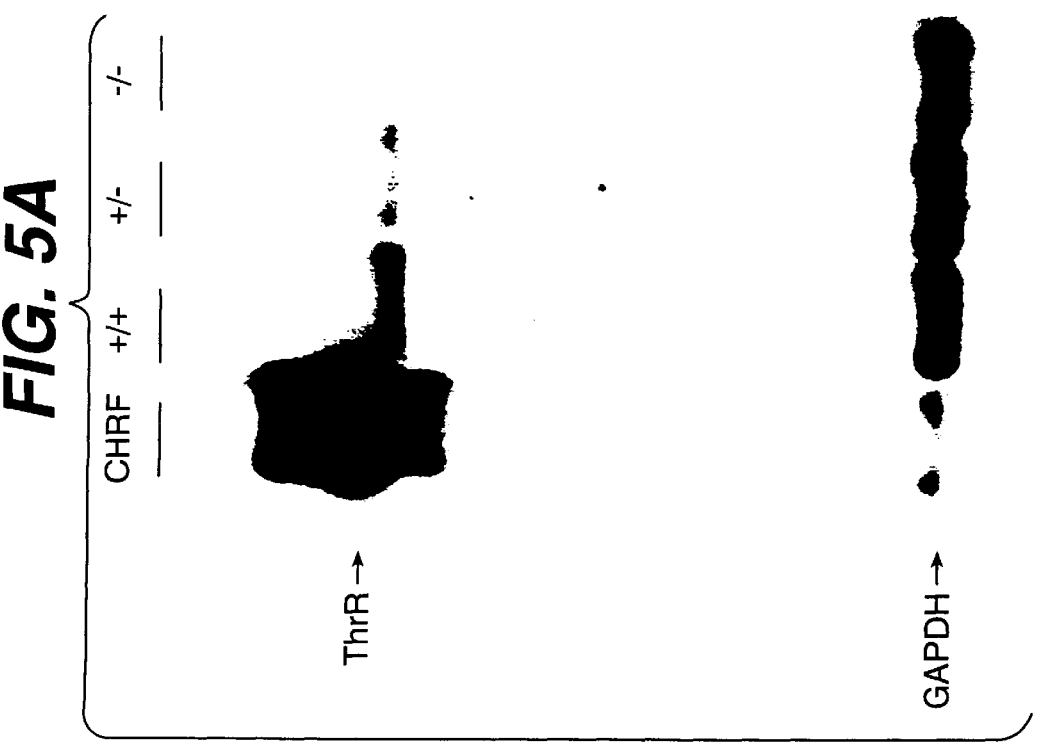

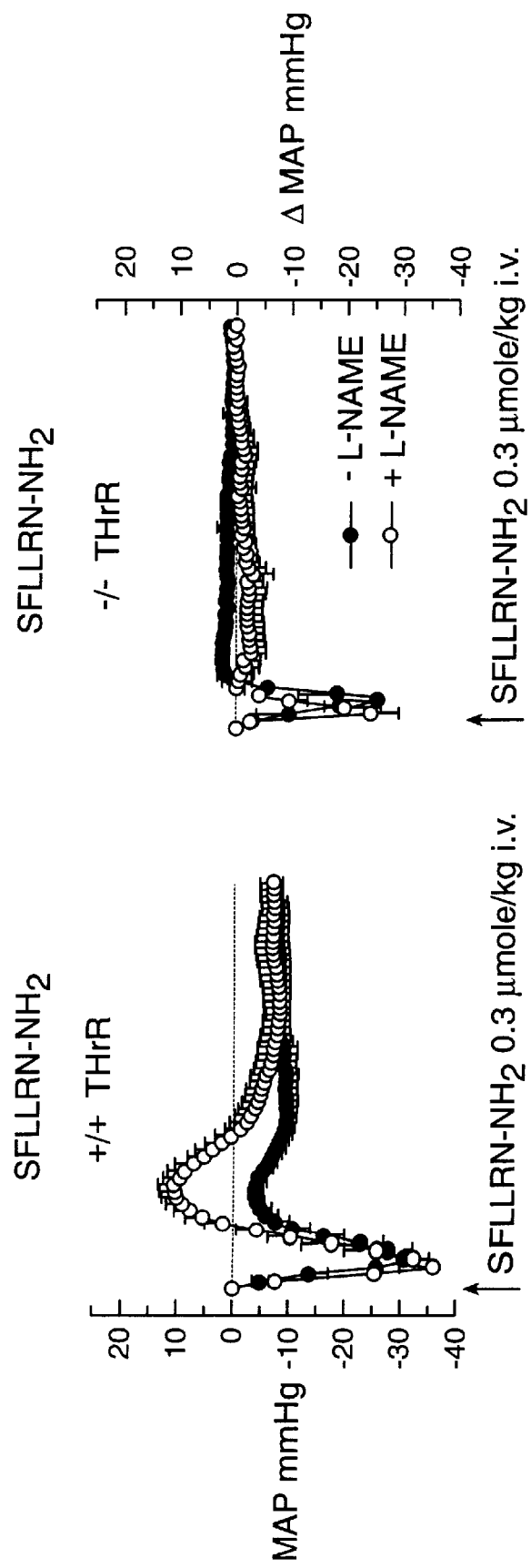

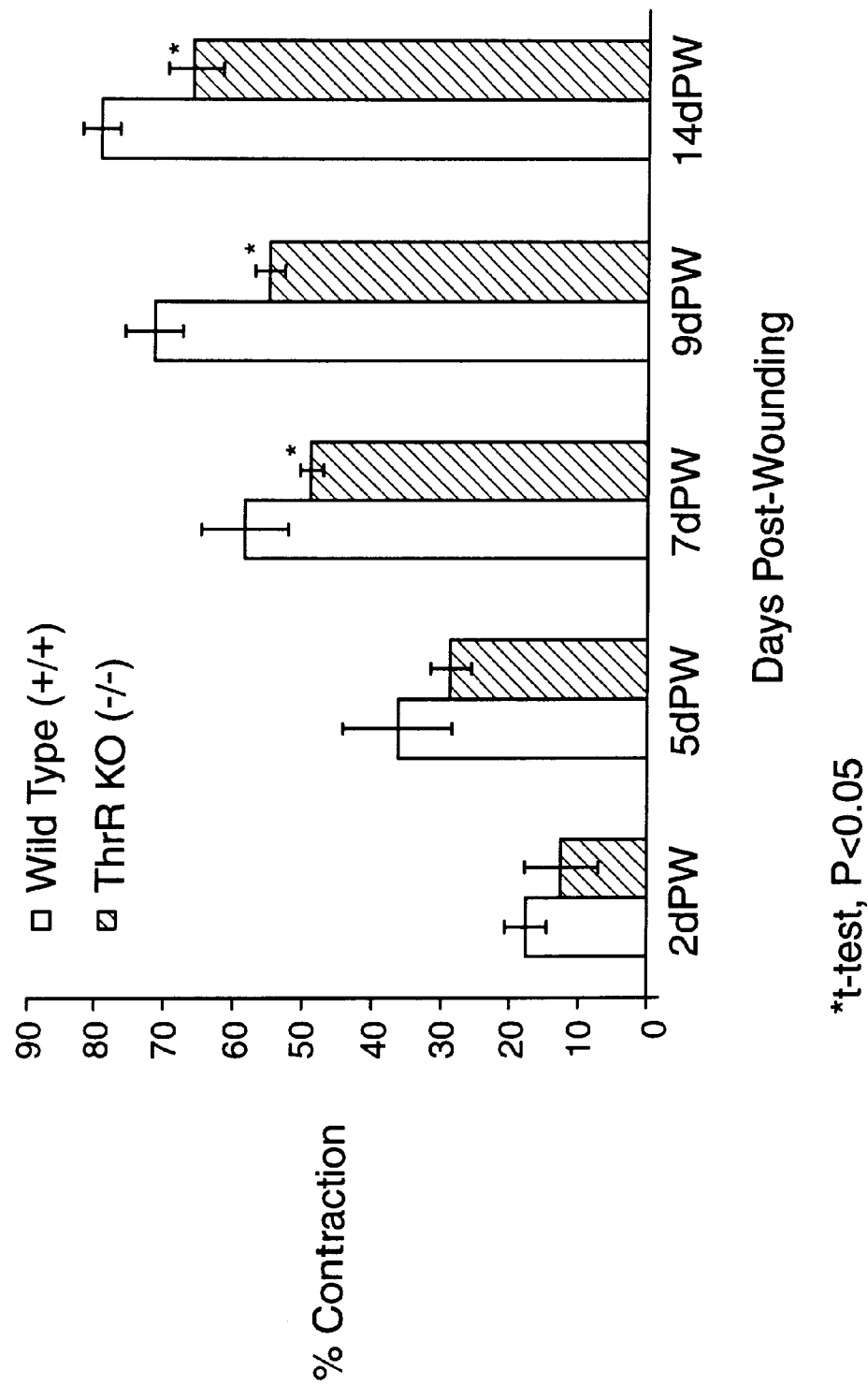

even in the presence of more cleaved/activated receptor. Graded responses to thrombin appear to be generated from a balance of receptor activation rate and second messenger clearance. Notably, this hypothesis indicates that an antagonist of the thrombin receptor must only slow down the rate of receptor activation in order to block signaling.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: double
      (D) TOPOLOGY: linear (ii) MOLECULE TYPE: cDNA (iv) ANTI-SENSE: NO (xi) SEQUENCE DESCRIPTION: SEQ ID NO:1:

TTCTTACATG TGGGAGCACC GAAG                          24

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: double
      (D) TOPOLOGY: linear (ii) MOLECULE TYPE: cDNA (iv) ANTI-SENSE: NO (xi) SEQUENCE DESCRIPTION: SEQ ID NO:2:

GCCAAGTTCT AATTCCATCA G                                                 221

(2) INFORMATION FOR SEQ ID NO:3:

(i) SEQUENCE CHARACTERISTICS:
            (A) LENGTH: 35 base pairs
            (B) TYPE: nucleic acid
            (C) STRANDEDNESS: double
            (D) TOPOLOGY: linear (ii) MOLECULE TYPE: cDNA (iv) ANTI-SENSE: NO (xi) SEQUENCE DESCRIPTION: SEQ ID NO:3:

TTTACAGGCT ACGCCTCTGC TTTGGAGAAA AGAGA                                   335

(2) INFORMATION FOR SEQ ID NO:4:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iv) ANTI-SENSE: NO (xi) SEQUENCE DESCRIPTION: SEQ ID NO:4:

Ser Phe Leu Leu Arg Asn
1               5

(2) INFORMATION FOR SEQ ID NO:5:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iv) ANTI-SENSE: NO (xi) SEQUENCE DESCRIPTION: SEQ ID NO:5:

Phe Ser Leu Leu Arg Asn
1               5

THROMBIN RECEPTOR DEFICIENT TRANSGENIC MICE

This application claims benefit of provisional application 60/016,070, filed Apr. 23, 1996 and provisional application 60/020,544, filed Jun. 25, 1996.

FIELD OF THE INVENTION

The present invention relates to transgenic nonhuman animals wherein a thrombin receptor gene is altered, producing an animal lacking functional thrombin receptor.

BACKGROUND OF THE INVENTION

The cloning of a platelet thrombin receptor has provided a framework to understand how thrombin interacts with cells, and has suggested a new target for antithrombotic and other therapies (Coughlin, S. R.; Scarborough, R. M.; Vu, T.-K. H.; Hung, D. T. (1992) Thrombin Receptor Structure and Function. Cold Spring Harbor Symposia on Quantitative Biology 57, 149–154; Coughlin, S. R.; Vu, T.-K. H.; Hung, D. T.; Wheaton, V. I. (1992) Expression Cloning and Characterization of a Functional Thrombin Receptor Structure Reveals a Novel Proteolytic Mechanism of Receptor Activation. Semin. Thromb. Haemostasis 18, 161–166). The first thrombin receptor to be cloned and sequenced was that from a human megakaryocytoblastoma cell line (Vu et al., 1991, infra). This human "platelet" receptor was expressed in different cell types, such as Chinese hamster ovary (CHO) cells, and appears capable of mediating standard cellular responses to thrombin (calcium flux, phosphoinositide turnover, cell proliferation). The thrombin receptor has also been cloned and sequenced for other mammalian cell types. Amino acid sequences of functional thrombin receptors from human platelets (Vu, T.-K. H., Hung, D. T., Wheaton, V. I., Coughlin, S. R. (1991) Molecular Cloning of the Functional Thrombin Receptor Reveals a Novel Proteolytic Mechanism of Receptor Activation. Cell 64, 1057–1068.), Chinese hamster lung fibroblasts (Rasmussen, U. B., et al. (1991) cDNA Cloning and Expression of a Hamster a-Thrombin Receptor Coupled to $Ca^{2+}$ Mobilization. FEBS Lett., 288, 123–128), rat vascular smooth muscle cell (Zhong, C.; Hayzer, D. J.; Corson, M. A.; Runge, M. S. (1992) Molecular Cloning of the Rat Vascular Smooth Muscle Thrombin Receptor. Evidence for In Vitro Regulation by Basic Fibroblast Growth Factor. J. Biol. Chem. 267, 16975–16979), and mouse osteoblastic cells (Tanaka, H.; Suva, L. J.; Suong, L. T.; Rodan, G. A. (1993) Cloning of the Mouse Thrombin Receptor from Osteoblastic Cells and Regulation of its Expression by 1,25-Dihydroxyvitamin $D_3$ and Parathyroid Hormone. J. Bone Mineral Res. Abstr. 108.) were derived from cDNA cloning and found to have a high degree of homology.

Structural analysis of the protein sequence revealed that the thrombin receptor is a member of the G-protein coupled receptor (GPCR) superfamily, with seven transmembrane (TM) domains, an extracellular amino terminus, and a cytoplasmic carboxy terminus. A guanine nucleotide-binding protein, which is key to cytoplasmic signal transduction, probably associates with intracellular loops 2 and 3, and the carboxy terminus. Thrombin proteolytically cleaves the long extracellular amino terminus between Arg-41 and Ser-42 to expose a new amino terminus which functions as a tethered peptide ligand for a yet-unknown recognition domain in the body of the receptor that induces receptor activation (Vu, T.-K. H.; Hung, D. T.; Wheaton, V. I.; Coughlin, S. R. (1991) Molecular Cloning of the Functional Thrombin Receptor Reveals a Novel Proteolytic Mechanism of Receptor Activation. Cell 64, 1057–1068). Thus the thrombin receptor is unique among GPCR's in that its activating ligand is self-contained, rather than generated separately as a hormone or transmitter.

The model of receptor-thrombin interaction, receptor cleavage, and signal transduction has been supported by studies with structural variants of the receptor and specific peptides (Vu, T.-K. H.; Wheaton, V. I.; Hung, D. T.; Charo, I.; Coughlin, S. R. (1991) Domians Specifying Thrombin-Receptor Interaction. Nature 353, 674–677), and monoclonal antibodies (Brass, L. F. (1992) Homologous Desensitization of HEL Cell Thrombin Receptors. J. Biol. Chem. 267, 6044–6050; Bahou, W. F.; Coller, B. SW.; Potter, C. L.; Norton, K. J.; Kutok, J. L.; Goligorsky, M. S. (1993) The Thrombin Receptor Extracellular Domain Contains Sites Crucial for Peptide-Ligand-Induced Activation. J. Clin. Invest. 91, 1405–1413; Norton, K. J.; Scarborough, R. M.; Kutok, J. L.; Escobedo, M.-A.; Nannizzi, L.; Coller, B. S. (1993) Immunologic Analysis of the Cloned Platelet Thrombin Receptor Activation Mechanism: Evidence Supporting Receptor Cleavage, Release of the N-Termianl Peptide, and Insertion of the Tethered Ligand into a Protected Environment. Blood 82, 2125–2136). Studies with mutant thrombin receptors have shown that cleavage of the N-terminus of the receptor is necessary for activation. Mutations in the tethered ligand domain inhibit activation of the expressed receptor (Scarborough, R. M., et al. (1992) Tethered Ligand Agonist Peptides: Structural Requirments for Thrombin Receptor Activation Reveal Mechanism of Proteolytic Unmasking of Agonist Function. J. Biol. Chem. 267, 13146–13149).

The unique mechanism for proteolytic receptor activation also raises a long standing question about thrombin-cell interaction. How are thrombin cellular responses elicited in a classical, concentration-dependent, ligand-receptor mechanism rather than through enzyme-based activity? In fact, the rate of receptor cleavage is proportional to thrombin concentration (Hung, D. T.; Vu, T.-K. H.; Nelken, N. A.; Coughlin, S. R. (1992) Thrombin-Induced Events in Non-Platelet Cells are Mediated by the Unique Proteolytic Mechanism Established for the Platelet Thrombin Receptor. J. Cell Biol. 116, 827– 832.). However, low concentrations of thrombin ultimately cleave and activate all thrombin receptors. Hence, a novel shut-off mechanism to deal with the "irreversibility" nature of the tethered ligand must exist within the cell, in particular, because shut-off can occur despite the continued presence of cleaved/activated receptor. Cumulative phosphoinositide hydrolysis in response to thrombin correlates precisely with cumulative receptor cleavage as a function of time (Ishii, K.; Hein, L.; Kobilka, B.; Coughlin, S. R. (1993) Kinetics of Thrombin Receptor Cleavage on Intact Cells. Relation to Signaling. J. Biol. Chem. 268, 9780–9786). These data strongly suggest generation of a "quantum" of second messenger by each activated thrombin receptor before shut-off, which continues Thrombin receptor is expressed in many different cell types including platelets, endothelial cells, smooth muscle cells, osteoblasts, fibroblasts, lymphocytes, neurons, and astrocytes.

SUMMARY OF THE INVENTION

To understand the functional role of thrombin receptor in different cell types, mice that do not express the functional thrombin receptor were generated by homologous recombination (HR) in embryonic stem (ES) cells and are disclosed herein. These mice provide a valuable animal model to understand the function of thrombin receptor and to evaluate the therapeutic effects of drugs that modulate the function or the expression of thrombin receptor in human cells.

BRIEF DESCRIPTION OF THE DRAWINGS

FIG. 1 shows the locations of the oligonucleotides MTR-1, -2, -3 and -5 in the mouse thrombin receptor cDNA sequence (GenBank, accession number L03529). These oligonucleotides were used in gene cloning. Arrows indicate orientations of the oligonucleotides.

FIG. 5 Panels A and B Northern blotting analysis confirming ThrR gene disruption is shown. Two parallel blots were run with 2.5 mg of pA$^+$ kidney RNA from +/+, +/−, and −/− mice, and probed individually with the hThrR cDNA (ThrR) (A) or with part of the neomycin coding region (Neo) (B) and exposed to film. Total CHRF megakaryocytic cell RNA (5 mg) was included on the Northern blot in A as a size marker of ThrR mRNA. Following exposure, the blots were reprobed with GAPDH for normalization.

FIG. 9 shows the rate and quality of wound healing in the +/+ and −/− ThrR mice.

DETAILED DESCRIPTION OF THE INVENTION

Figure 2:
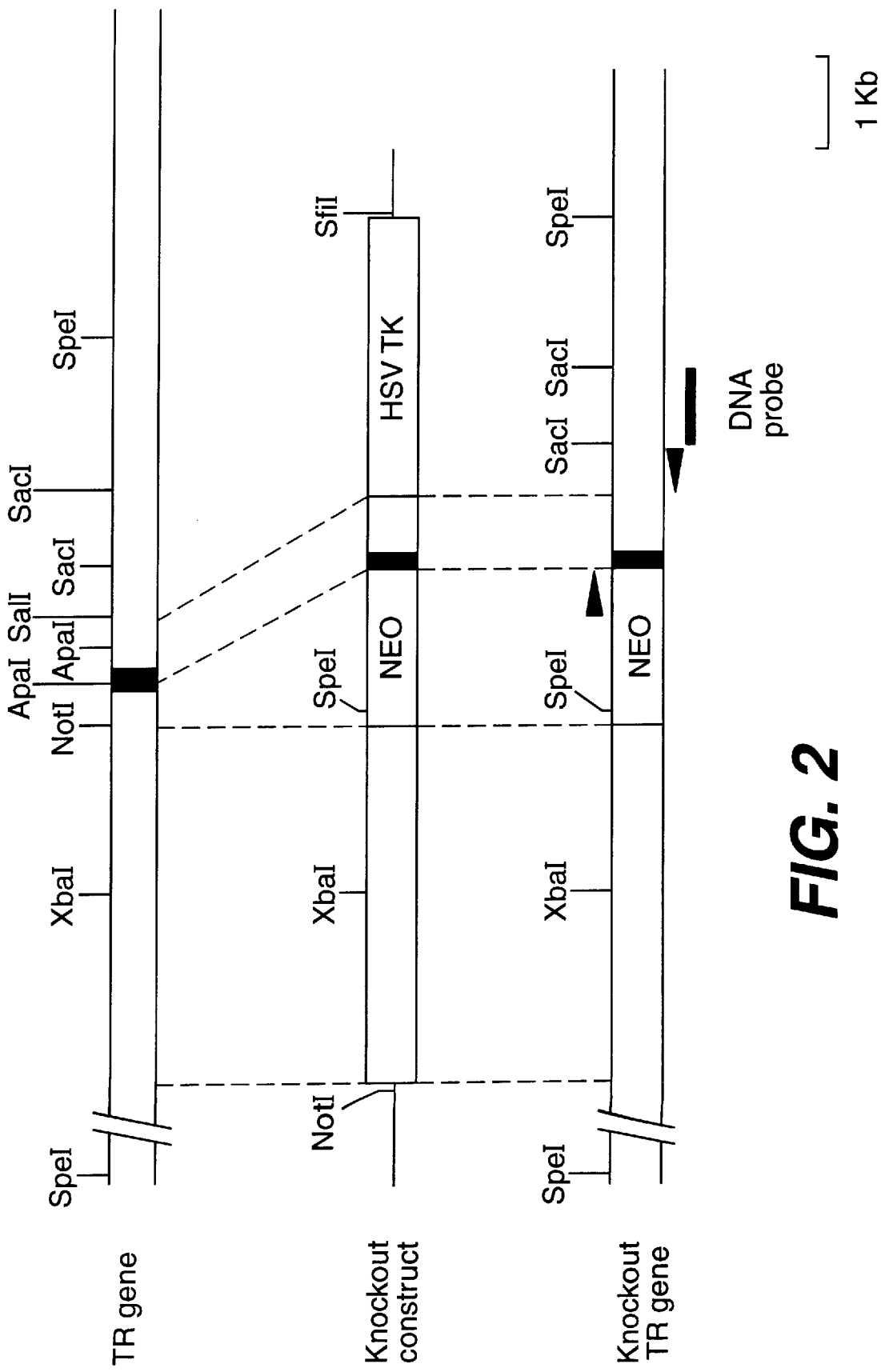
FIG. 2 shows a genomic map of the mouse thrombin receptor gene contained in the murine genomic clone, the knockout DNA construct, and the disrupted thrombin receptor gene after homologous recombination with the construct. The neomycin resistance gene (NEO) and the HSV tk gene (HSV TK) in the construct are shown. The 0.8 Kb region between the two SacI sites was used as a DNA probe in Southern hybridization.

The thrombin receptor knockout mice that were generated provide a model in which the thrombin receptor-gene was disrupted by homologous recombination (HR). The process of generating the knockout mice can be divided into 4 basic stages:

1. cloning of the thrombin receptor gene and preparation of DNA construct for transfection of embryonic stem (ES) cells;
2. isolating ES cells in which the thrombin receptor gene has been disrupted by HR;
3. generating chimeric mice from mouse embryos injected with the knockout ES cells; and
4. breeding chimeric mice to obtain knockout mice through germline transmission.

The present invention utilizes a cloned genomic DNA encoding the thrombin receptor protein and describes the cloning and characterization of the mouse thrombin receptor gene. Transgenic animals are generated which have altered the thrombin receptor gene. The alterations to the naturally occurring gene can be modifications, deletions and substitutions. Modifications and deletions render the naturally occurring gene nonfunctional, producing a "knockout" animal. Substitution of the naturally occurring gene for a gene from a second species results in an animal which produces the gene product of the second species. Substitution of the naturally occurring gene for a gene having a mutation results in an animal which produces the mutated gene product. These transgenic animals are critical for drug antagonist or agonist studies, the creation of animal models of human diseases, and for eventual treatment of disorders or diseases associated with human thrombin receptor-mediated responses. A transgenic animal carrying a "knockout" of the thrombin receptor is useful for the establishment of a nonhuman model for diseases involving thrombin receptor equivalents in the human.

A transgenic mouse carrying the disrupted thrombin receptor gene was generated by homologous recombination of a target DNA construct with the endogenous gene in the chromosome. The DNA construct was prepared from a genomic clone of the thrombin receptor which was isolated from a genomic DNA library derived from the 129 SV mouse strain.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass classical cross-breeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact possess some or all of that alteration or genetic information, they are transgenic animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The altered thrombin receptor gene generally should not fully encode the same thrombin receptor as native to the host animal, and its expression product should be altered to a minor or great degree, or absent altogether. However, it is conceivable that a more modestly modified thrombin receptor gene will fall within the scope of the present invention.

The genes used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro [M. J. Evans et al., Nature 292: 154–156 (1981); M. O. Bradley et al., Nature 309: 255–258 (1984); Gossler et al. Proc. Natl. Acad. Sci. USA 83: 9065–9069 (1986); Robertson et al., Nature 322, 445–448 (1986); S. A. Wood et al. Proc. Natl. Acad. Sci. USA 90: 4582–4584 (1993)]. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, Science 240: 1468–1474 (1988)).

Since thrombin receptor is an independent component of a complex mechanism, the proteins, including that encoded by thrombin receptor DNA, must be examined both individually and as a group if their contribution to the mechanisms are to be understood. One approach to the problem of determining the contributions of individual genes and their expression products is to use isolated genes to selectively inactivate the native wild-type gene in totipotent ES cells (such as those described herein) and then generate transgenic mice. The use of gene-targeted ES cells in the generation of gene-targeted transgenic mice was described in 1987 (Thomas et al., Cell 51:503–512, (1987)) and is reviewed elsewhere (Frohman et al., Cell 56:145–147 (1989); Capecchi, Trends in Genet. 5:70–76 (1989); Baribault et al., Mol. Biol. Med. 6:481–492, (1989); Wagner, EMBO J. 9: 3025–3032 (1990); Bradley et al., Bio/Technology 10: 534–539 (1992)).

Techniques are available to inactivate or alter any genetic region to any mutation desired by using targeted homologous recombination to insert specific changes into chromosomal genes. Homologous recombination was reported to be detected at frequencies between $10^{-6}$ and $10^{-3}$ (Lin et al., Proc. Natl. Acad. Sci. USA 82:1391–1395 (1985); Smithies et al., Nature 317: 230–234 (1985); Thomas et al., Cell 44:419–428, (1986); Song et al., Proc. Natl. Acad. Sci. USA 84:6820–6824 (1987)). Nonhomologous plasmid-chromosome interactions are more frequent, occurring at levels $10^5$-fold (Lin et al., Proc. Natl. Acad. Sci. USA 82:1391–1395 (1985)) to $10^2$-fold (Thomas et al., Cell 44:419–428 (1986); Song et al., Proc. Natl. Acad. Sci. USA 84:6820–6824 (1987)) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., Nucleic Acids Res. 16:8887–8903 (1988); Kim et al., Gene 103:227–233 (1991)). Alternatively, a positive genetic selection approach has been developed in which a marker gene is constructed which will only be active if homologous insertion occurs, allowing these recombinants to be selected directly (Sedivy et al., Proc. Natl. Acad. Sci. USA 86:227–231 (1989)). One of the most powerful approaches developed for selecting homologous recombinants is the positive-negative selection (PNS) method developed for genes (such as thrombin receptor) for which no direct selection of the alteration exists (Mansour et al., Nature 336:348–352: (1988); Capecchi, Science 244:1288–1292, (1989); Capecchi, Trends in Genet. 5:70–76 (1989)). The PNS method is more efficient for targeting genes which are not expressed at high levels because the marker gene has its own promoter. Nonhomologous recombinants are selected against by using the Herpes Simplex virus thymidine kinase (HSV-TK) gene flanking the DNA construct. Cells with nonhomologous insertion of the construct express HSV thymidine kinase and therefore are sensitive to the herpes drugs such as gancyclovir (GANC) or FIAU (1-(2-deoxy 2-fluoro-B-D-arabinofluranosyl)-5-iodouracil). By this counter-selection, the number of homologous recombinants in the surviving transformants can be increased.

As used herein, a "targeted gene" or "knockout" is a DNA sequence introduced into the germline of a non-human animal by way of human intervention, including but not limited to, the methods described herein. The targeted genes of the invention include DNA sequences which are designed to specifically alter cognate endogenouos genes.

There are many members of the GPCR that have afforded potent agonist and/or antagonist ligands, and this has been a basis for important drugs, such as propranolol (beta-adrenergic antagonist), prazosin (alpha-adrenergic-1 antagonist), cimetidine (histamine-2 antagonist), fentanyl (opiate agonist), haloperidol (dopamine-2 antagonist), sumatripan (serotonin-1 agonist), risperifone (dopamine-2/serotonin-2 antagonist), and ondansetron (serotonin-3 antagonist). With this perspective, it is eminently reasonable to pursue thrombin receptor agonists and antagonists. Furthermore, the thrombin receptor might represent a prototype of a diverse class of receptors activated by enzyme-based proteolysis.

The development of thrombin receptor modulators can be used in a wide range of therapeutic applications. This include cardiovascular problems resulting from percutaneous transluminal coronary angioplasty, coronary artery-bypass grafting, myocardial infarction, restenosis, transient ischemic attacks, strokes, angina and atherosclerosis. Thrombin receptor antagonist will limit platelet adhesion and prevent thrombosis and restenosis during acute interventional procedures. It would be more effective than aspirin and would in some cases likely be used concurrently with aspirin. The market for these clinical indications is enormous and the medical needs are still largely unmet, as indicated by mortality and morbidity statistics.

A thrombin receptor agonist is projected to be useful in wound repair based on the proliferative effect of thrombin receptor on fibroblasts. There is a need for novel wound care therapies that accelerate wound repair and treat recalcitrant ulcers. The treatment of diabetic ulcers and stasis ulcers representing a very large area of unmet medical need.

Thrombin inhibits the outgrowth of neurites. With a thrombin receptor antagonist, one would seek an Alzheimer's therapy to arrest the underlying progression of the disease and its characteristic symptomatology, CNS trauma therapies aimed at stroke, spinal injury and head trauma. There is a dearth of effective therapies in the area of neurodegenerative diseases. Both Alzheimer's and CNS trauma rank very high in terms of unmet medical need.

Given the effect of thrombin in bone resorption processes, the possibility exists for the treatment of bone degenerative diseases. The effect of thrombin on neutrophil adhesion and other cellular response to tissue damage may also open new avenues for the treatment of inflammation.

All the above applications have to be verified in animal tests and eventually clinical trials. One approach to determine the functional role of the drug target is to study the defects resulting from the disrupted gene in a whole animal. The thrombin receptor knockout mice that have been generated and are disclosed herein will allow the definition of the function of thrombin receptor which is critical in deciding the types of modulators most suitable in therapies.

In Search of Novel Thrombin Receptors with the Knockout Mice

Human platelet aggregation can simply be induced by treatment with a hexapeptide, the amino acid sequence of which corresponds to the new amino terminus of the receptor after thrombin cleavage. However, this peptide fails to activate platelets in several species such as rat, hamster and rabbit (Cook, N. S.; Günter-Hans, Z.; Tapparelli, M. P.; Singh, J.; Metternich, R.; Hagenbach, A. (1993) Platelet Aggregation and Fibrinogen Binding in Human, Rhesus Monkey, Guinea Pig, Hamster and Rat Blood: Activation by ADP and a Thrombin Receptor Peptide and Inhibition by Glycoprotein IIb/IIIa Antagonists. Thromb. Haemostasis 70, 531–539.; Kinlough-Rathbone, R. L.; Rand, M. L.; Packham, M. A. (1993) Rabbit and Rat Platelets Do Not Respond to Thrombin Receptor Peptides that Activate Human Platelets. Blood 82, 103–106; Catalfamo, J. L.; Andersen, T. T.; Fenton, J. W., II. (1993) Thrombin Receptor-Activating Peptides Unlike Thrombin are Insufficient for Platelet Activation in Most Species. Thromb. Haemostasis 69, 1195, Abstr. 2331; Connolly, T. M.; Condra, C.; Feng, D.-M.; Reilly, C. F.; Nutt, R. F.; Gould, R. J. (1993) Species Variability in Platelet Responsiveness to Thrombin Receptor-Derived Peptides. Thromb. Haemostasis 69, 706, Abstr. 595.; Derian, C. K.; Santulli, R. J.; Tomko, K. A.; Haertlein, B. J.; Andrade-Gordon, P. (1995) Species Differences in Platelet Responses to Thrombin and SFLLRN. Receptor-Mediated Calcium Mobilization and Aggregation and Regulation by Protein Kinases. Thromb. Res. 78, 505–519). Conversely, the agonist peptides have different effects in different cell types even in the same species. For example, the hexapeptide fails to induce rat platelet aggregation (Kinlough-Rathbone et al., 1993, supra), although it produces contractile activity in rat vascular smooth muscle and increases intracellular $Ca^{++}$ in rat aortic smooth muscle cells (Antonaccio, M. J.; Normandin, D.; Serafino, R.: Moreland, S. (1993) Effects of Thrombin and Thrombin Receptor Activating Peptides on Rat Aortic Vascular Smooth Muscle. J. Pharmacol. Exp. Ther. 266, 125–132). Thus, it seems likely that the human platelet-derived thrombin receptor, as defined by Vu et al., does not mediate all of the biological activities of thrombin in many cell types and in diverse mammalian species. The existence of alternative receptors or receptor subtypes, or the presence of different G-protein coupling mechanisms distinct to cell type, is possible (Hollenberg, M. D.; Laniyonu, A. A.; Saifeddine, M.; Moore, G. J. (1993) Role of the Amino- and Carboxyl-Terminal Domains of Thrombin Receptor-Derived Polypeptides in Biological Activity in Vascular Endothelium and Gastric Smooth Muscle: Evidence for Receptor Subtypes. Mol. Pharmacol. 43, 921–930.). Any thrombin receptor function that is detected in the knockout mice of the present invention would provide evidence of the existence of alternative novel thrombin receptor subtypes which may then be isolated from the knockout mice of the present invention.

The absence of functional thrombin receptor in the knockout mice of the present invention are confirmed in RNA analysis, protein expression detection, receptor binding assays and other receptor functional studies. For RNA analysis, RNA samples are prepared from different organs of the knockout mice and the thrombin receptor transcript are detected in Northern blots using oligonucleotide probes specific for the transcript.

Polyserum and monoclonal antibodies that are specific for the mouse thrombin receptor are produced. The absence of intact thrombin receptor in the knockout mice are studied in flow cytometric analysis, in immunohistochemical staining, and in receptor binding assays using thrombin receptor-specific antibodies. Alternatively, receptor binding assays are performed using labeled peptides to bind to membrane preparations of different cell types collected from the knockout mice.

Defining the Function of Thrombin Receptor in Platelet Activation with the Knockout Mice The best characterized receptor function of a-thrombin is the activation of platelets. Thrombin is the most potent stimulator known of platelet aggregation and degranulation. Thrombin may also be the most significant mediator of platelet recruitment in arterial thrombus formation. Platelets, which play a key role in thrombus formation and hemostasis, respond to thrombin in a dose-dependent manner. The process of thrombin-induced platelet activation is initiated by proteolytic cleavage of the thrombin receptor. However, the role of thrombin receptor activation in human thrombosis and hemostasis has not been clearly demonstrated because of a lack of specific pharmacological agents to interrupt receptor function and a lack of knowledge about possible thrombin receptor genetic diseases. The only in vivo studies of a thrombin receptor blocker were reported by COR Therapeutics (Lindahl, A. K.; Scarborough, R. M.; Naughton, M. A.; Harker, L. A.; Hanson, S. R. (1993) Antithrombotic Effect of a Thrombin Receptor Antagonist Peptide in Baboons. Thromb. Haemostasis 69, 1196, Abstr. 2333.) and Merck Research Laboratories (Cook, J. J., Sitko, G. R., Bednar, B., Condra, C., Mellot, M. J., Feng, D.-M., Nutt, R. F., Shafer, J. A., Gould, R. J., Connolly, T. M. (1995) An Antibody Against the Exosite of the Cloned Thrombin Receptor Inhibits Experimental Arterial Thrombosis in the African Green Monkey. Circulation 91, 2061–2971). The COR study used a weak hexapeptide-based antagonist, C186-65, which was found to moderately inhibit platelet deposition in a Dacron graft arteriovenous shunt model (baboons) after infusion. The Merck study used an antibody against the exosite of the cloned thrombin receptor which was used to demonstrate that blockade of the platelet thrombin receptor can prevent arterial thrombosis in the African green monkey without significantly altering hemostatic parameters. The knockout mice without expression of the thrombin receptor that that are the subject of thie present invention, will allow definition of the function of this receptor and to assess the therapeutic effects of thrombin receptor agonists or antagonists. The pursuit of thrombin receptor antagonist is particularly valuable in thrombotic disorders. Antithrombotic agents inhibit or modulate the enzymatic activity of thrombin, thereby blocking all functions of the enzyme in the hemostatic pathway. By contrast, an antagonist to the receptor could specifically inhibit receptor mediated cellular responses, leaving the hemostatic-clotting balance untouched.

Thrombin is one of the most effective agonists of platelet activation. Platelets have been used to study thrombin-dependent signal transduction and thrombin-induced cell functions by measuring different parameters such as aggregation, degranulation, secretion, calcium mobilization and induction of P-selectin expression. Platelet aggregation in whole blood samples can be studied and aggregation can be measured by light transmission in an aggregometer. A new procedure to study platelet aggregation has been set up in platelet-rich plasma from rats that utilizes g-thrombin. g-Thrombin, unlike a-thrombin (its precursor), does not recognize fibrinogen as a substrate, making it incapable of producing fibrin clots. The tests described above are performed to assess platelet function from platelets collected from the knockout mice that are devoid of the thrombin receptor.

Animal models of platelet adhesion and thrombosis are approximations of human pathology. In human, endothelial dysfunction, chronic atherosclerosis, and plaque fissuring are central components of arterial thrombosis (Fuster, V.; Badimon, L.; Badimon, J. J.; Chesebro, J. H. (1992) The Pathogenesis of Coronary Artery Disease and the Acute Coronary Syndromes. New Engl. J. Med. 326, 242–250.). Most animal models of arterial thrombosis involve acute injury to the blood vessel or contact of blood with thrombogenic surface (arteriovenous shunts), ultimately leading to the generation of thrombin. The injury stimulus may be electrical current (Schumacher, W. A.; Steinbacher, T. E.; Heran, C. L.; Megill, J. R., Durham, S. K. (1993) Effects of Antithrombotic Drugs in a Rat Model of Aspirin-Insensitive Arterial Thrombosis. Thromb. Haemostasis 70, 509–514.), ferric chloride (Kurz, K. D.; Main, B. W.; Sandusky, G. E. (1990) Rat Model of Arterial Thrombosis Induced by Ferric Chloride. Thromb. Res. 60, 269–280), or mechanical damage (Roux, S.; Carteaux, J. P.; Hess, P.; Falivene, L.; Clozel, J. P. (1994) Experimental Carotid Thrombosis in the Guinea Pig. Thromb. Haemostasis 71, 252–256.), leading to activation of the extrinsic (tissue factor) pathway of thrombin generation. These in vivo assays are performed in the knockout mice of the present invention.

Defining the Function of Thrombin Receptor in Activation of Endothelial Cells with the Knockout Mice Thrombin activation of endothelial cells is known to induce the secretion of products that can alter hemostatic mechanisms, including platelet derived growth factor, von Willebrand factor, prostacyclin, tPA, and tPA inhibitor. Thrombin is also known to increase the adhesive proteins on the outer membrane. Thrombin rapidly upregulates P-selectin (GMP-140), a component of the Weibel-Palade body in endothelial cells and of the granules in platelets (McEver, R. P.; Beckstead, J. H.; Moore, K. L.; Marshall-Carlson, L.; Bainton, D. F. (1989) GMP-140, a Platelet a-Granule Membrane Protein, is also Synthesized by Vascular Endothelial Cells and is Localized in Weibel-Palade Bodies. J. Clin. Invest. 84, 92–99.; Sugama, Y.; Tiruppathi, C.; Janakidevi, K,: Andersen, T. T.; Fenton, J. W., II; Malik, A. B. (1992) Thrombin-Induced Expression of Endothelial P-Selectin and Intercellular Adhesion Molecule-1: A Mechanism for Stabilizing Neutrophil Adhesion. J. Cell Biol. 119, 935–944). P-selectin is translocated to the endothelial cell membrane, where it rapidly induces polymorphonuclear leukocyte (PMN) adhesion. The activation of endothelial cells by thrombin therefore enhance infiltration and extravasation of PMN into the inflammatory sites. Thrombin activation of endothelial cells collected from the knockout mice of the present invention are studied by the induction of P-selection detected in flow cytometry, and the trigger of cell proliferation measured in thymidine uptake experiments. The thrombin receptor-induced secretion by endothelial cells of tPA, PAI, PDGF, and prostacyclin are also studied.

Defining the Function of Thrombin Receptor in Smooth Muscle Cell Proliferation and Contraction with the Knockout Mice Medial smooth muscle cells (SMC) migrate and proliferate into the intima in response to chemoattractants and growth factors, released at the site of vascular injury. This process has been considered a major contributor to the proliferation and progression of atherosclerotic lesions and post-angioplastic restenosis. Such lesions are often occluded by a growing thrombus, which becomes a source of thrombin activity. The potential role of thrombin in the vicinity of SMC has placed emphasis on the mitogenic role of thrombin in SMC proliferation. Indeed, enzymatically competent thrombin, and thrombin receptor tethered ligand derived peptides (TRAPs) have full efficacy in stimulating rat aortic SMC proliferation in culture. Northern blot analysis shows the expression of thrombin receptor also in SMC in human atherosclerotic plaques (Nelken, N.; Soifer, S.; O'Keefe, J.; Vu, T.-K.; Charo, I.; Coughlin, S. (1992) Thrombin Receptor Expression in Normal and Atherosclerotic Human Arteries. J. Clin. Invest. 90, 1614–1621.). Receptor antagonists might contribute to limiting thrombin-stimulated SMC proliferation associated with restenosis or atherogenesis. The challenge is to define the role of the thrombin receptor in normal physiology and in disease states. The knockout mice of the present invention are useful for this purpose. From that, a potential treatment for atherosclerosis may be possible (Ross, R. (1993) the Pathogenesis of Atherosclerosis: A Perspective for the 1990s. Nature 362, 801–809). The thrombin receptor deficient animals of the present invention are also useful as an in vivo model for restenosis.

The generation of thrombin in the vicinity of the vessel wall makes it a candidate for local regulation of vasomotor tone during injury and acute thrombotic syndromes. The action of thrombin on vascular tone is complex, involving endothelium-dependent relaxation and endothelium-independent contraction. Canine coronary arteries and saphenous veins with intact endothelium respond to a-thrombin or TRAPs with dose-dependent relaxation (Tesfamariam, B.; Allen, G. T.; Normandin, D.; Antonaccio, M. J. (1993) Involvement of the "Tethered Ligand" Receptor in Thrombin-Induced Endothelium-Mediated Relaxations. Am. J. Physiol. 265, H1744–H1749.; Ku, D. D.; Zaleski, J. K. (1993) Receptor Mechanism of Thrombin-Induced Endothelium-Dependent and Endothelium-Independent Coronary Vascular Effects in Dogs. J. Cardiovasc. Pharmacol. 22, 609–616.). Thrombin and TRAPs have been shown to release prostacyclin from cultured endothelial cells (Ngaiza, J. R.; Jaffe, E. A. (1991) A 14-Amino Acid Peptide Derived from the Amino Terminus of the Cleaved Thrombin Receptor Elevates Intracellular Calcium and Stimulates Prostacyclin Production in Human Endothelial Cell. Biochem. Biophys. Res. Commun. 179, 1656–1661.) and endothelial nitric oxide, a potent relaxant of smooth muscle (Antonaccio et al., 1993, supra). This might be counterbalanced by the production of endothelin, a potent vasoconstrictor (Yanagisawa, M. et al. (1988) A Novel Potent Vasoconstrictor Peptide Produced by Vascular Endothelial Cell. Nature 332, 411–415). In the absence of endothelium, thrombin and TRAPs mediate direct vasoconstriction (Walz, D. A.; Anderson, G. F.; Ciaglowski, R. E.; Aiken, M.; Fenton, J. W., II (1985) Thrombin-Elicited Contractile Responses of Aortic Smooth Muscle. Proc. Soc. Exp. Biol. Med. 180, 518–526.; Muramatsu, I.; Laniyonu, A.; Moore, G. J.; Hollenberg, M. D. (1992) Vascular Actions of Thrombin Receptor Peptide. Can. J. Physiol. Pharmacol. 70, 996–1003.) presumably by increasing intracellular calcium release, as demonstrated in cultured vascular smooth muscle cells (Antonaccio et al., 1993, supra). Thrombin stimulates cardiac contractility in amphibian and avian hearts by increasing intracellular calcium with concurrent elevation in contractile force, rate, and action-potential duration (Markwardt, F.; Franke, T.; Glusa, E.; Nilius, B. (1990) Pharmacological Modification of Mechanical and Electrical Responses of Frog Heart to Thrombin. Pflugers Arch. 412, 668–670.; Chien, W. W.; Mohabir, R.; Clusin, W. T. (1990) Effect of Thrombin on Calcium Homeostasis in Chick Embryonic Heart Cells. J. Clin. Invest. 85, 1436–1443.). In mammalian cardiac myocytes, thrombin induces formation of inositol triphosphate ($IP_3$), increases cytosolic Ca(II), and enhances automaticity (Steinberg, S. F.; Robinson, R. B.; Lieberman, H. B.; Stern, D. M.; Rosen, M. R. (1991) Thrombin Modulates Phosphoinositide Metabolism, Cytosolic Calcium, and Impulse Initiation in the Heart. Circulation Res. 68, 1216–1229.). Thrombin may also contribute to abnormalities in cardiac rhythm during ischemic episodes.

A quantitative method for studying thrombin receptor-dependent smooth muscle agonist and antagonist activity in rat aortic rings has been developed from a modification of the method described by Antonaccio et al. (1993), supra. Isolated buffer-perfused rings of vascular smooth muscle are a functionally integrated system for studying the role of thrombin receptor on smooth muscle cells. The thoracic aorta is collected from the knockout mice of the present invention, cut into rings, endothelialized or de-endothelialized, and mounted in perfusion chambers. The contraction or relaxation response of the muscle rings to thrombin or the agonist peptides is then measured. Other smooth muscle under neurogenic control such as mouse ileum are studied to ascertain if functional thrombin receptors exist in peripheral nerve terminals. This would constitute an important modulatory role for the receptor in nervous tissue. The integrated physiological response of Langendorff heart to thrombin is also studied in organ perfusion experiments. a-Thrombin would elicit a dose-dependent reduction in left-ventricular-developed pressure and ventricular contractility, and would increase coronary perfusion pressure without affecting myocardial conduction. Other organs derived from the knockout mice of the present invention such as lung, kidney and vascular beds are used in the perfused organ experiments. Any defective responses observed in organs from knockout mice would be an indication of the thrombin receptor function in different organs. Vascular smooth muscle cells from the knockout mice of the present invention are used to study whether cell proliferation can be triggered by thrombin without the expression of thrombin receptor. This system will serve as an in vitro model for restenosis.

Defining the Role of Thrombin Receptor in Neuronal Cell Growth with the Knockout Mice Considerable evidence is rapidly accumulating indicating the importance of thrombin in the central nervous system, particularly neurodegeneration. Early reports of thrombin's actions on neuronal cells were its ability to stimulate proliferation and morphological changes in glial cells (Perraud F, Besnard F, Sensenbrenner M, Labourdette G (1987) Thrombin is a potent mitogen for rat astropblasts but not for oligodendroblasts and neuroblasts in primary culture. Int. J. Dev. Neurosci. 5, 181–188.; Loret C, Sensenbrenner M, Labourdette G (1989) Differential phenotypic expression induced in cultured rat astroblasts by acidic fibroblast growth factor, epidermal growth factor and thrombin. J.Biol. Chem. 264, 8319–8327; Cavanaugh KP., Gurwitz D., Cunningham DD, Bradshaw RA (1990) Reciprocal modulation of astrocyte stellation by thrombin and protease nexin-1. J. Neurochem. 54, 1735–1743), cause neurite retraction (Gurwitz D and Cunningham DD (1988) Thrombin modulates and reverses neuroblastoma neurite outgrowth. Proc. Natl. Acad. Sci. USA 85, 3440–3444; Gurwitz, D.; Cunningham, D. D. (1988) Thrombin Modulates and Reverses Neuroblastoma Neurite Outgrowth. Proc. Natl. Acad. Sci. USA 85, 3440–3444.; Zurn et al., 1988, Grabham PW, Monard D, Gallimore PH, Grand RJA (1991) Modulation of human neurite outgrowth by serine proteases: a comparison of the interaction of thrombin and prothrombin with glia-derived nexin. Eur. J. Neurosci. 3, 663–668.; Suidan et al., 1992), induce the release of arachidonic acid from spinal cord cultures (Means ED and Anderson DK (1986) Thrombin interactions with central nervous system tissue and implications of these interactions. Ann NY Acad. Sci. 485, 314–322.) and rapidly stimulate Ca+ dependent cGMP formation in neuroblastoma cells (Snider and Richelson, 1983). In addition, thrombin receptors were discovered in the brain and spinal cord on both neurons and astrocytes (McKinney M, Snider RM, Richelson E (1983) Thrombin binding to human brain and spinal cord. Mayo Clin. Proc. 58, 829–831; Means and Anderson, 1986, supra; Rasmussen et al., 1991, supra; Vu et al., 1991a, supra; Suidan et al., 1992; Weinstain et al., 1995). The presence of thrombin receptors was intriguing since thrombin is not normally found in the brain parenchyma. Nevertheless, recent evidence indicates that prothrombin RNA is found in the brain (Dihanich, M.; Kaser, M.:; Reinhard, E.; Cunningham, D.; Monard, D. (1991) Prothrombin mRNA is Expressed by Cells of the Nervous System. Neuron 6, 575–581) and both prothrombin and thrombin have been shown in cerebrospinal fluid (Festoff BW, Rao JS, Chen M (1992) Protease nexin-1, thrombin- and urokinase-inhibiting serpin, concentrated in normal human cerebrospinal fluid. Neurology 42, 1361–1366). How prothrombin is converted to thrombin in the brain remains to be determined. Several studies indicate that thrombin levels increase dramatically in the brain after injury. Suzuki et al., (1994) reported that traumatic brain injury results in increased levels of thrombin in the brain up to five-fold, In addition, Nishino et al., (Nishino A, Suzuki M, Motohashi O, Umezawa K, Nagura H, Yoshimoto T (1993) Thrombin may contribute to the pathophysiology of central nervous system injury. J. Neurotrauma 10, 167–179) demonstrated that intracerebral injections of thrombin resulted in infiltration of inflammatory cells, proliferation of mesenchymal cells, induction of angiogenesis, increased vascular permeability and increased vimentin-positive astrocytes. The source of increased thrombin in brain injury may be vascular (i.e., cerebral infarct), but also may include endogenous thrombin produced in situ in response to brain injury. Moreover, it has been reported that thrombin and thrombin complexed with endogenous inhibitors (e.g., protease nexin-1 (PN-1)) is elevated in neurodegenerative disease states such as Alzheimer's disease and cerebral ischemia (Wagner et al., 1989; Akiyama H., Skeda K., Kondo H., McGreer P L (1992) Thrombin accumulation in brains of patients wth Alzheimer's disease. Neurosci. Lett. 146, 152–154; Davies T A, Fine RE, Johnson R J, Levesque C A, Rathbun W H, Seetoo K F, Smith S J, Strohmeier G, Volicer L, Delva L, Simons E R (1993) Non-age related differences in thrombin responses by platelets from male patients with advanced Alzheimer's disease. Biochem. Biophys. Res. Commun. 194, 537–543).

The thrombin receptor knockout mouse model of the present invention offers a unique means to examine the importance of thrombin in neuronal injury. Energy deprivation and excitotoxicity are believed to contribute to neuronal injury in both acute and chronic neurodegenerative disorders. For example, in both cerebral ischemia and traumatic brain injury, cellular ATP levels are reduced (Martin R L, Lloyd H G E, Cowan A I (1994) The early events of oxygen and glucose deprivation: setting the scene for neuronal death? Trends Neurosci. 17, 251–257), and glucose availability appears reduced in Alzheimer's disease (Hoyer, S., 1988, Glucose And Related Brain Metabolism In Dimentia Of Alzheimer Type And Its Morphological Significance, Age, 11, pp. 158–166). In such brain injuries, levels of thrombin and its endogenous inhibitors (e.g., PN-1) are increased to varying amounts, and therefore it is important to understand how they influence the injury process. Recent evidence demonstrated that thrombin is neurotoxic to cultured hippocampal neurons in a concentration-dependent manner (Smith-Swintosky et al., 1995, Protease Nexin 1 And Thrombin Modulate Neuronal Ca Homeostasis And Sensitivity To Glucose Deprivation-induced Injury, J.Neurosci., 15, pp. 5840–5850). Moreover, subtoxic levels of thrombin exacerbate several metabolic/excitoxic insults such as glucose deprivation-induced damage, glutamate toxicity and b-amyloid toxicity in hippocampal cultures (Smith-Swintosky et al., 1995, Protease Nexin 1 And Thrombin Modulate Neuronal Ca Homeostasis And Sensitivity To Glucose Deprivation-induced Injury, J.Neurosci., 15, pp. 5840–5850; Smith-Swintosky et al., 1995, Opposing Actions Of Thrombin And Protease Nexin-1 On Amyloid b-Peptide Toxicity And On Accumulation Of Peroxides And Calcium In Hippocampal Neurons, J.Neurochem., 65, pp.1415–1418). Hippocampal and cortical cells cultured from the knockout mice of the present invention are used to determine whether they respond to these insults in a similar manner or prove to be more resistant to neurotoxicity due to the lack of the thrombin receptor. The results of these studies will indicate the relative importance of thrombin in the cell death accompanying these insults and establish an in vivo model of neurodegeneration, such as cerebral ischemia and excitotoxicity.

Defining the Role of Thrombin Receptor in Fibroblast Proliferation and Tissue Repair with the Knockout Mice Recent data support the initial observation that thrombin induces fibroblast proliferation via thrombin receptor activation, to transmit mitogenic signals. The agonistic peptides TRAPs are potent and efficacious mitogens of CCL39 cells, a Chinese hamster fibroblast line (Hung, D. T.; Vu, T.-K. H.; Nelken, N. A.; Coughlin, S. R. (1992) Thrombin-Induced Events in Non-Platelet Cells are Mediated by the Unique Proteolytic Mechanism Established for the Platelet Thrombin Receptor. J. Cell Biol. 116, 827–832.; Reilly, C. F.; Connolly, T. M.; Feng, D. M.; Nutt, R. F.; Mayer, E. J. (1993) Thrombin Receptor Agonist Peptide Induction of Mitogenesis in CCL39 Cells. Biochem. Biophys. Res. Commun. 190, 1001–1008). Fibroblasts are a good initial cell-based model for potential applications in wound healing. Studies of the actions of thrombin on different cell types involved in the early and late stages of wound healing have indicated a role for thrombin in tissue repair. Thrombin can initiate effects related to wound healing, such as: increasing vascular permeability to allow entry of cells and fluid into injured tissue (Malik, A. B. (1986) Thrombin-induced Endothelial Injury. Semin. Thromb. Haemostasis 12, 184–196.); increasing the synthesis of PDGF by endothelial cells (Harlan, J. M.; Thompson, P. J.; Ross, R. R.; Bowen-Pope, D. F. (1986) a-Thrombin Induces Release of Platelet-Derived Growth Factor-Like Molecule(s) by Cultured Human Endothelial Cells. J. Cell Biol. 103, 1129–1133); increasing adhesion of platelets, monocytes, and neutrophils to endothelial cells (Carney, D. H. (1992) Postclotting Cellular Effects of Thrombin Mediated by Interaction with High-Affinity Thrombin Receptors. Thrombin: Structure and Function, Berliner, L. J., Ed.; Plenum Press: New York, pp 351–396.; Bevilacqua, M. P.; Stengelin, S.; Gimbrone, M. A. J.; Seed, B. (1989) Endothelial Leukocyte Adhesion Molecule 1: An Inducible Receptor for Neutrophils Related to Complement Regulatory Proteins and Lectins. Science 243, 1160–1165; Saegusa, Y.; Cavender, D.; Ziff, M. (1988) Stimulation of Mononuclear Cell Binding to Human Endothelial Cell Monolayers by Thrombin. J. Immunol. 141, 4140–4145); and increasing the proliferative response of endothelial cells (Zetter, B. R.; Antoniades, H. N. (1979) Stimualtion of Human Vascular Endothelial Cell Growth by Platelet Derived Growth Factor and Thrombin. J. Supramol. Struct. 11, 361–370.), smooth muscle cells, and fibroblasts (Chen, L. B.; Buchanan, J. M. (1975) Mitogenic Activity of Blood Components I. Thrombin and Prothrombin. Proc. Natl. Acad. Sci. USA 72, 1311–1315; Perez-Rodriguez, R.; Franchi, A.; Pousségur, J. (1978) Growth Factor Requirements of Chinese Hamster Lung Fibroblasts in Serum Free Media: High Mitogenic Reaction of Thrombin. Cell Biol. Intl. Rep. 5, 347–357; Pohjanpelto, P. (1977) Proteases Stimulate Proliferation of Human Fibroblasts. J. Cell. Physiol. 91, 387–392). Recently, the presence of a functional thrombin receptor in human epidermal keratinocytes was demonstrated (Santulli, R. J., Derian, C. K., Darrow A. L., Tomko, K. A., Eckardt, A. J., Seiberg, M., Scarborough, R. M., Andrade-Gordon, P. (1995) Evidence for the Presence of a Protease-Activated Receptor Distinct from the Thrombin Receptor in Human Keratinocytes. Proc. Natl. Acad. Sci. USA 92, 9151–9155). These cells actively participate in skin tissue repair or pathology.

Cell proliferation responses by thrombin are tools to explore thrombin receptor's role in tissue damage and repair mechanisms. For agonist-based fibroblast proliferation studies, fresh serum-free media with stimulus was added to the cells and incubated overnight. Cells were pulsed with $^3$H-thymidine and uptake of thymidine was measured. Tissue repair following a surgical incision in rats is promoted by the use of a-thrombin (Carney et al., 1992, supra). The possibility to accelerate normal wound healing with receptor agonist peptides presents a new option for the management of wound healing. The knockout mice of the present invention are used to analyze the ability of these animals to accelerate wound repairs after injuries exposed to either thrombin or agonistic peptides such as TRAPs.

Defining the Role of Thrombin Receptor in Cellular Chemotaxis with the Knockout Mice Thrombin has been implicated in a variety of inflammatory responses to tissue damage. Thrombin is chemotactic for human peripheral blood monocytes (Bar-Shavit, R.; Kahn, A.; Wilner, G. D. (1983) Monocyte Chemotaxis: Stimulation by Specific Exosite Region in Thrombin. Science 220, 728–730) and mitogenic for lymphocytes (Chen, L. B.; Teng, N. N. H.; Buchanan, M. (1976) Mitogenicity of Thrombin and Surface Alteration on Mouse Splenocytes. Exp. Cell Res. 101, 41–46). Thrombin also induces neutrophil adhesion to the vessel wall via an endothelium-dependent mechanism (Zimmerman, G. A.; McIntyre, T. M.; Prescott, S. M. (1986) Thrombin Stimualtes Neutrophil Adherence by an Endothelial Cell-Dependent Mechanism. Ann. NY Acad. Sci. 485, 349–368), by inducing production of the adhesion protein P-selectin from endothelial cells. Accumulation of neutrophils may lead to release of toxic oxygen radicals and proteases that potentiate tissue damage, and induce reperfusion injury. Neutrophils isolated from the knockout mice can be used to explore the role of thrombin receptor in cellular chemotaxis.

Defining the Role of Thrombin Receptor in Bone Cell Growth with the Knockout Mice Bone degenerative diseases are caused by either increased bone resorption or decreased bone formation. Thrombin causes bone resorption in vitro by prostaglandin-dependent and -independent pathways (Lerner, U. H.; Gustafson, G. T. (1988) Blood Coagulation and Bone Metabolism: Some Characteristics of the Bone Resorptive Effect of Thrombin in Mouse Calvarial Bones In Vitro. Biochim. Biophys. Acta 964, 309–318). Moreover, rapid changes in phosphoinositide metabolism may play a second-messenger role in thrombin-stimulated bone resorption (Stern, P. H.; Stathopoulos, V. M.; Shankar, G.; Fenton, J. W., II (1990) Second Messengers in Thrombin-Stimulated Bone Resorption. J Bone Mineral Res. 5, 443–449). This is a typical intracellular signal caused by a G-protein-dependent 7-transmembrane receptor, such as the thrombin receptor. Thrombin has been implicated in osteoblast proliferation, phosphoinositide turnover, and increased cytosolic calcium levels. These actions were directly inhibited in a dose-dependent manner by hirudin, a potent and selective thrombin inhibitor (Tatakis, D. N.; Dolce, C.; Dziak, R.; Fenton, J. W. (1991) Thrombin's Effects on Osteoblastic Cells. II. Structure-Function Relationships. Biochem. Biophys. Res. Commun. 174, 181–188). TRAPs have been reported to elicit calcium-phospholipid signaling pathways in an osteoblastic cell system (Jenkins, A. L.; Bootman, M. D.; Taylor, C. W.; Mackie, E. J.; Stone, S. (1993) Characterization of the Receptor Responsible for Thrombin Intracellular Calcium Responses in Osteoblastic-like Cells. J. Biol. Chem. 268, 21433–21437). Furthermore, the thrombin receptor from osteoblastic mouse cell lines was cloned, and studies of thrombin receptor mRNA regulation showed high expression in the proliferative phase and a gradual decrease after confluence of the cells (Tanaka, H.; Suva, L. J.; Suong, L. T.; Rodan, G. A. (1993) Cloning of the Mouse Thrombin Receptor from Osteoblastic Cells and Regulation of its Expression by 1,25-Dihydroxyvitamin $D_3$ and Parathyroid Hormone. J. Bone Mineral Res. Abstr. 108). Modulation of the function of thrombin receptor may be a suitable target for the treatment of pathological degenerative bone diseases. Bone cells from the knockout mice of the present invention are prepared and the thrombin receptor-dependent proliferation is studied to evaluate the involvement of thrombin receptor in cellular response.

The following Examples are presented for the purpose of illustrating the present invention and are not to be construed as a limitation on the scope of this invention.

EXAMPLE 1

Cloning of the Thrombin Receptor Gene

A 129 SV mouse genomic library in a lambda phage vector was screened for genomic clones containing the thrombin receptor gene. Initial screen of the library utilized a PCR-amplified DNA probe derived from the sequence of the mouse thrombin receptor (available from GenBank, accession number L03529). The probe which covers nucleotide 612 to 1312 of the thrombin receptor cDNA was amplified by PCR using oligonucleotides MTR-2 and MTR-3 (shown in FIG. 1), $P^{32}$-labeled and used for screening 300,000 plaque forming units from the library. One of the two clones isolated was further analyzed. It was found at this point that the 15 Kb genomic DNA fragment did not contain the 5' end of the gene, which is a preferred insertion site for disruption of a functional gene. $3 \times 10^5$ plaque forming units from the same library was then screened again using the two oligonucleotide probes (MTR-1 and MTR-5; FIG. 1) covering the 5' end sequence of the cDNA. Two clones were isolated from the screen and one of the clones was further characterized as shown in FIG. 2.

EXAMPLE 2

Preparation of DNA Construct for the Thrombin Receptor Gene

A 4.8 Kb DNA fragment within the thrombin receptor gene clone was used to prepare a knockout DNA construct. This region covered a 4 Kb of the 5' flanking region up to the the NotI site of the gene, and a 0.8 Kb region covering part of exon 1 and intron 1 of the thrombin receptor gene (FIG. 2). A 0.4 Kb NotI-ApaI DNA fragment in the gene which covers the promoter region as well as part of exon 1 including the first ATG codon of the open reading frame was deleted in the construct. The neo cassette containing the neomycin resistant gene was placed into the ApaI site in exon 1 with orientation the same as the thrombin receptor gene. The Herpes simplex virus type-1 thymidine kinase (HSV tk) gene was placed at the 3' end of the homologous region. Therefore the knockout construct contains a neomycin resistance gene, a 4.8 Kb region homologous to the thrombin receptor gene and a HSV tk gene at the 3' end. The final DNA construct was created in the plasmid backbone pUC18 with two rare cloning sites placed at both ends of the construct, a NotI site at the 5' end and a SfiI site at the 3' end.

EXAMPLE 3

Transfection of ES Cells with the Thrombin Receptor DNA Constructs

The final DNA construct of Example 2 was linearized by complete digestion with either NotI or SfiI, or a combination of both. DNA was then precipitated by 2 volumes of ice cold ethanol at -20_C. for 1 hour. Precipitated DNA was pelletted by centrifugation, rinsed once with 0.5 ml 70% ethanol, air dried and then dissolved at 1 mg/ml in phosphate-buffered saline (Gibco).

Embryonic stem (ES) cells E14 (Hooper et al., 1987, HPRT-deficient (Lesch-Nyhan) mouse embryos derived from germline colonization by cultured cells. Nature 326, 292–295) were maintained at an undifferentiated stage by co-culturing with embryonic fibroblasts (EF) and in culture medium DMEM (15% FCS, 1 mM sodium pyruvate, 0.1 mM b-mercaptoethanol, 2 mM L-glutamine, 100 U penicillin and 100 U streptomycin) containing 1000 U/ml leukemia inhibitory factor (LIF) (Gibco). EF cells were primary fibroblast cultures prepared from day 15–17 mouse fetuses according to the method described by Robertson (Robertson, E. J. (1987) Embryo-derived Stem Cell Lines. In: Teratocarcinomas and Embryonic Stem Cells. E. J. Robertson, ed. (Oxford, Washington DC: IRL Press), p 71–112.). EF were treated with 10 mg/ml mitomycin C (Sigma) in culture medium for 2 hours to stop cell division prior to the use as feeder cells. For DNA transfection, ES cells were harvested by trypsin treatment and resuspended at $6.25 \times 10^6$ cell/ml in culture medium. DNA construct (20 mg) was added to 0.8 ml of ES cell suspension for electroporation at 250 mF and 340 Volts using the Gene Pulser (BioRad).

Transfected ES cells were plated onto EF coated 90 mm plates at $2.5 \times 10^6$/plate in culture medium. Two days later, cells were subjected to drug selection in medium containing 400 mg/ml G418 (Geneticin, Gibco) and 2 mM GANC (Cytosin, Syntex). Culture medium was changed daily. Massive cell death was obvious starting day 4 and most of the dead cells were removed through daily medium change. Surviving cell colonies were observable under microscope by day 7 and by day 10 they were visible on the plates without a microscope.

PCR Screen of Transfected ES Cells for Homologous Recombination

The size of ES colonies on day 11 after transfection was large enough for PCR screening. To collect cell colonies, culture medium in the 90 mm plates was aspirated and 10 ml PBS was added. Individual cell colonies were located with the aid of a stereomicroscope, collected in a 20 ml volume with an autopipetteman and transferred into 96 well-plates. To prepare single cell suspension of the ES colonies, 25 μl of 0.25% trypsin (Gibco) was added per well in 96 well-plates. After 8 minutes of trypsin treatment at 37_C., 25 μl of culture medium was added. All the ES colonies were still maintained in culture as master plates while screening by PCR for homologous recombination events was performed. To prepare master plates, 60 μl of each cell sample was transferred to 96-well plates which had been coated with EF cells and contained 180 μl/well of the culture medium containing G418 and GANC.

For the first round PCR screen, each cell lysate sample was prepared from 12 cell colonies which arrayed as one row of samples in the 96 well-plates. After the preparation of master plates, the remaining cell samples of about 90 μl/well on every row of the plates were pooled. Cells were pelleted in tubes by centrifugation for 1 minute. After draining all the medium, cells were lysed by adding 30 μl distilled water and brief vortexing. Cell lysates were prepared by first heating at 95_C. for 10 minutes, cooling to room temperature and followed by an addition of 1 ml proteinase K (10 mg/ml in water) with brief vortexing, a 90 minute incubation at 50_C. for proteinase K digestion, and then 10 minutes at 95_C. for heat inactivation of proteinase K.

PCR was carried out using the 9600 GeneAmp system (Perkin Elmer). The reaction mixtures contained 5 μl cell lysate, 4 μM of each of the two oligonucleotide primers, 200 μM each of dATP, dTTP, dCTP, and dGTP, and 5 U Ampli-Taq DNA polymerase in PCR buffer (10 mM Tris-Cl, pH8.3, 50 mM KCl, 1.5 mM MgCl$_2$ and 0.001% w/v gelatin). The reaction condition was 3 cycles of 2 min at 94_C., 2 min at 60_C., and 2 min at 72_C., then 40 cycles of 15 sec at 94_C., 15 sec at 60_C., and 1 min at 72_C., followed by 7 min at 72_C.. PCR primers that were used to amplify homologous recombination were: TR11R (5'-TTCTTACATGTGGGAGCACCGAAG-3') [SEQ.ID.NO.:1] and neo-1858 (5'-GCCAAGTTCTAATTCCATCAG-3') [SEQ.ID.NO.:2] and the size of the amplified DNA is expected to be about 1 Kb.

To detect the specific DNA fragment amplified by PCR, 20 μl of the PCR samples were separated according to size by 1% agarose gel electrophoresis, blotted onto Hybond-N+ nylon membranes (Amersham), and hybridized to the P$^{32}$-labelled oligonucleotide probe TR10R (5'-TTACAGGCTACGCCTCTGCTTTGGAGAAAA GAGA-3') [SEQ.ID.NO.:3] which is located within the amplified DNA fragment as shown in FIG. 2. PCR samples with a 1 Kb DNA band detected by the oligo probe were considered as putative positive groups for further screening.

ES cells in master plates after 3–4 days culture were ready for splitting. Cell colonies in the positive groups were screened individually by a second round of PCR to identify the positive individual colonies. To maintain the positive groups in culture, cells in the wells were trypsinized by first removing the culture medium, rinsing once with 50 μl PBS, treating with 40 μl 0.25% trypsin for 5 minutes at 37_C., followed by adding 90 μl culture medium. Cells were then resuspended and 20 μl of the cell samples were transferred to master plates which had been coated with EF and filled with 200 μl culture medium containing G418 and GANC. The remaining cells (110 μl/well) were transferred into eppendorf tubes. Cell lysates were prepared and homologous recombination signals were amplified by PCR and detected by hybridization as described in the previous paragraphs.

Confirmation of Homologous Recombination by Genomic Southern Hybridization

Figure 3:
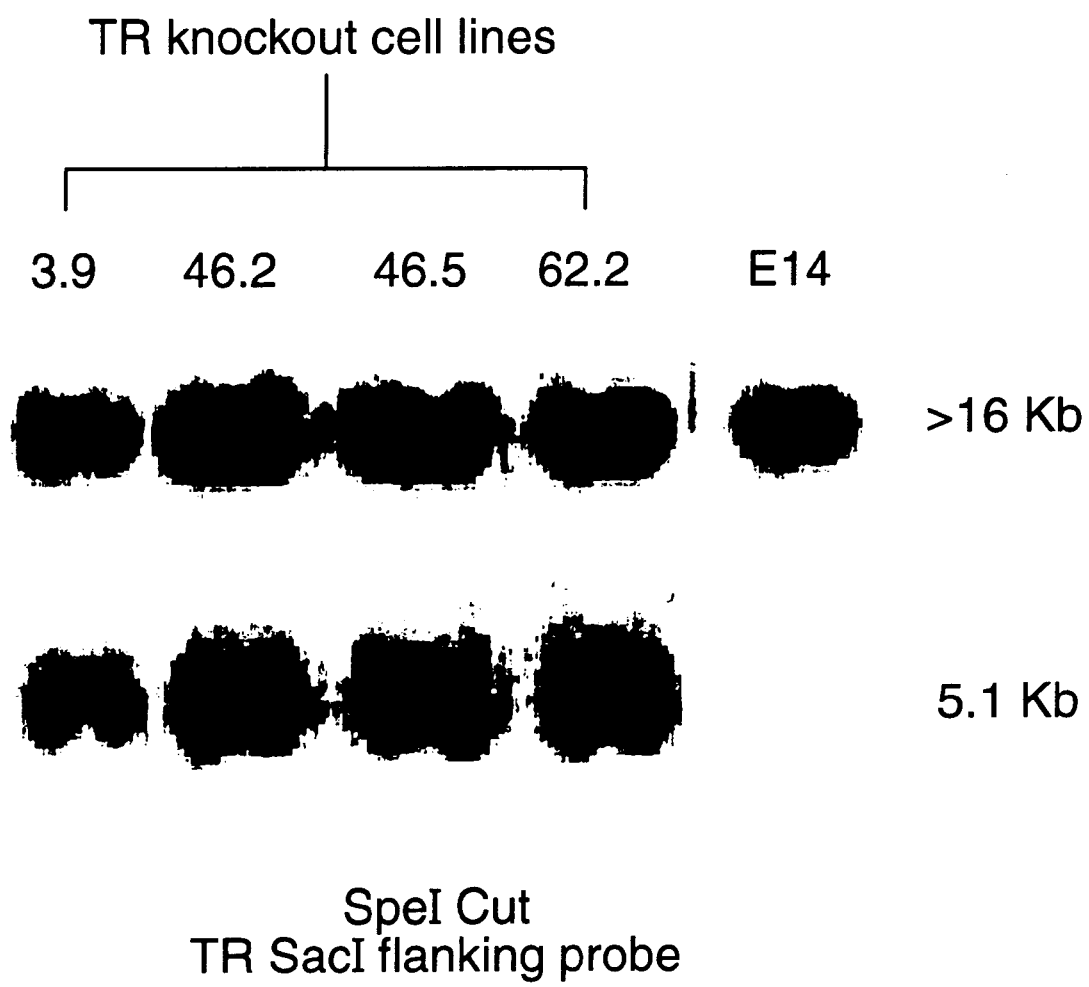
FIG. 3 shows a Southern hybridization analysis of targeted embryonic stem (ES) cell clones having the thrombin receptor knockout. Genomic DNA was digested with the restriction enzyme SpeI. The intact thrombin receptor gene was detected as a DNA band >16 Kb and the disrupted gene as a 5.1 Kb DNA band in hybridization using the 0.8 Kb SacI DNA fragment as a probe (shown in FIG. 2).

ES cells derived from the positive colonies in PCR screen were expanded in culture and DNA was extracted as described by Maniatis et al. (Maniatis, T.; Fritsch, E. F.; Sambrook, J. (1982) Molecular Cloning, Cold Spring Harbor Laboratory pp. 280–281). Genomic DNA samples of the putative knockout cell lines were digested with the restriction enzymes SpeI, separated by 1% agarose gel electrophoresis, blotted onto Hybond-N+nylon membranes (Amersham) and hybridized with the 0.8 kb SacI DNA fragment as shown in FIG. 2. This DNA probe did not hybridize to the DNA constructs that were integrated randomly in the chromosome. The normal thrombin receptor gene in chromosomal DNA was detected as a DNA band >16 Kb and the disrupted gene as a 5.1 Kb DNA band resulting from an additional SpeI site in the neomycin resistance gene (FIG. 2 and 3).

EXAMPLE 4

Generation of Chimeric Mice by Embryo Injection

Mouse embryos at 3.5 day gestation stage were collected from the uteri of superovulated C57BL/6J mice. The knockout cell lines that were used in embryo injections were: line 3.9, line 46.2, line 46.5 and line 62.2. About 10–15 ES cells were injected into the blastocoel cavity of the embryos. Injected embryos were transferred into the uteri of pseudopregnant CD1 mice at 2.5 day gestation. Mice developed from these embryos were born 17 days later. Since the ES cells used were derived from the 129 Ola mouse strain with the dominant agouti coat color genes, chimeric mice were identified by the agouti coat color from ES derived cells, versus the black color from C57BL/6J embryos.

EXAMPLE 5

ES Germline Mice Obtained by Chimeric Mouse Breeding

Chimeric mice were bred with C57BL/6J mice. These crosses are performed to test for the germline transmission of ES cells. Some of the progeny from the breeding are expected to be agouti if the chimeric male had germ line cells derived from ES cells which carry the dominant agouti coat color genes.

Figure 4:
FIG. 4 shows a Southern hybridization analysis of tail DNA from knockout mice. Patterns of DNA bands from mice that were wild type (+/+), heterozygous (+/−) and homozygous (−/−) for the disrupted thrombin receptor gene are shown. The intact thrombin receptor gene was detected as a DNA band >16 Kb and the disrupted gene as a 5.1 Kb DNA band in hybridization using the 0.8 Kb SacI DNA fragment as a probe (shown in FIG. 2).

Germline mice that were heterozygous for the disrupted thrombin receptor gene were identified by analysis of tail DNA in Southern hybridization as described in the previous paragraph. To determine the thrombin receptor genotypes, genomic DNA is purified from about 1 cm of tail from each agouti mouse after weaning. The genomic DNA is isolated as described (Laird et al., supra), followed by phenol and phenol:chloroform extractions and ethanol precipitation. Genomic DNAs are digested with SpeI, and hybridized with the 3' flanking DNA probes (shown in FIG. 2). Southern hybridization analysis confirms that the structure of the altered thrombin receptor gene is identical to that predicted, and previously characterized in the thrombin receptor targeted ES clones (FIG. 4).

EXAMPLE 6

Generation of Homozygous Knockout Mice from Breeding of Hetrozygous Knockout Mice Male and female heterozygous knockout mice, each of which contained one copy of the altered thrombin receptor gene, were mated with each other to generate mice in which both copies of the thrombin receptor gene are disrupted. It was predicted that one fourth of the mouse embryos would be homozygous for the altered thrombin receptor gene. Surviving offspring were genotyped by Southern hybridization as described above. Homozygous mutant mice are born at a ratio of 1 in 4 pups if the defective gene does not affect embryo development. Homozygous mutant mice were identified by analysis of tail DNA samples. DNA patterns of knockout mice are shown in FIG. 4. Only the 5.1 kb SpeI cut DNA band but not the large molecular (>16 kb) DNA band was observed for mice homozygous for the disrupted thrombin receptor gene. It was determined that 24 (7%, 16 males and 8 females) of the 323 offspring mice were homozygous thrombin receptor –/–, 103 (32%, 51 males and 52 females) were wild-type thrombin receptor +/+, and 196 (61%, 111 males and 85 females) were heterozygous thrombin receptor –/+.

A reduced proportion of –/– mice were produced and in addition, significant reductions in the percentage of female mice were detected within the surviving –/–, as well as the +/– groups. Similar results were obtained for three independent germlines, represented collectively in Table 1 below.

TABLE 1

Genotyping of offspring derived from +/– ThrR intercrosses.

| Genotype | N | % of Total* | Male:Female |
|----------|-----|-------------|-------------|
| +/+      | 107 | 30.5        | 0.95        |
| +/–      | 220 | 62.7        | 1.37†       |
| –/–      | 24  | 6.8         | 2.43†       |

*Significantly different from Mendelian ratio (50:25:25):$p < 0.0001$, $c^2$ test.
†Significantly different from +/+: $p < 0.01$, $c^2$ test.

There was no pronounced postnatal mortality associated with the –/– offspring. The surviving adult ThrR –/– mice appeared normal on gross anatomical and histological analysis. Furthermore, crosses between +/– and –/– ThrR mice resulted in smaller litters and fewer than the expected 50% –/– mice (6 –/– out of 35 pups). Matings between –/– ThrR mice occurred infrequently and generally produced less than three offspring. Embryonic resorption occured some time after embryonic day 10, implying that a large proportion of –/– embryos fail to develop in utero.

Northern blot experiments were performed to confirm the loss of ThrR gene expression in the surviving ThrR –/– mice (shown in FIG. 5). RNA was extracted from kidney of +/+, +/– and –/– ThrR mice or cultured CHRF-288-11 by using Trizol (Gibco/BRL, Gaithersburg, Md.). Poly A selection with biotinylated oligo dT and Streptavidin MagneSphere paramagnetic particles (Promega, Madison, Wis.) was carried out in combination with a magnetic particle concentrator (Dynal, Lake Success, N.Y.). Northern gel electrophoresis, transfer, and blot hybridizations were performed by established proce-dures [J. Sambrook, E. F. Fritsch, T. Maniatis, Molecular Cloning: A Laboratory Manual, 2nd edit., Cold Spring Harbor Laboratory Press, Cold Spring Harbor, N.Y. (1989)]. The ThrR probe consisted of the human ThrR coding sequences and the Neo probe was a 190-bp Pst I fragment. All probes were radiolabeled by random primer incorporation of $^{32}p$ dCTP (Gibco/BRL). Northern blots were subsequently probed by using human GAPDH sequences (Clontech, Palo Alto, Calif.) for normalization. Following hybridizations, the blots were washed at 60° C. twice in 2×SSC/0.1% SDS and twice in 0.5×SSC/0.1% SDS for 20 min/wash. The exposures were for four days with intensifying screens. As shown in FIG. 5A, the 3.4-kb ThrR transcript was reduced in RNA derived from +/– and diminished to undetectable levels in RNA from –/– mice. The neomycin (Neo) cassette, which was inserted in the same transcriptional orientation within the ThrR gene promoter and amino terminus of the coding sequence, was transcribed in +/– mice and this transcript was more abundant in –/– mice (FIG. 5B). On longer exposures, a low intensity band of approximately 4.5 kb was detected in –/– lanes probed with ThrR and Neo. The observation of this weak band is consistent with the generation of a low abundance Neo/ThrR fusion transcript which may have been generated by transcriptional read through and inefficient termination by the upstream mPGK-1 polyadenylation sequence within the Neo cassette. This analysis shows that: 1) the expression of the native ThrR mRNA was abolished in –/– mice; 2) an extremely low level of an altered Neo/ThrR fusion transcript, disrupted around the initiation methionine as determined by sequencing a subcloned RT/PCR product, may have been produced; and 3) the disrupted ThrR-coding sequence located downstream from the functional neomycin open-reading frame, within this altered transcript, was not translated into functionally significant amounts of protein.

Figure 6:
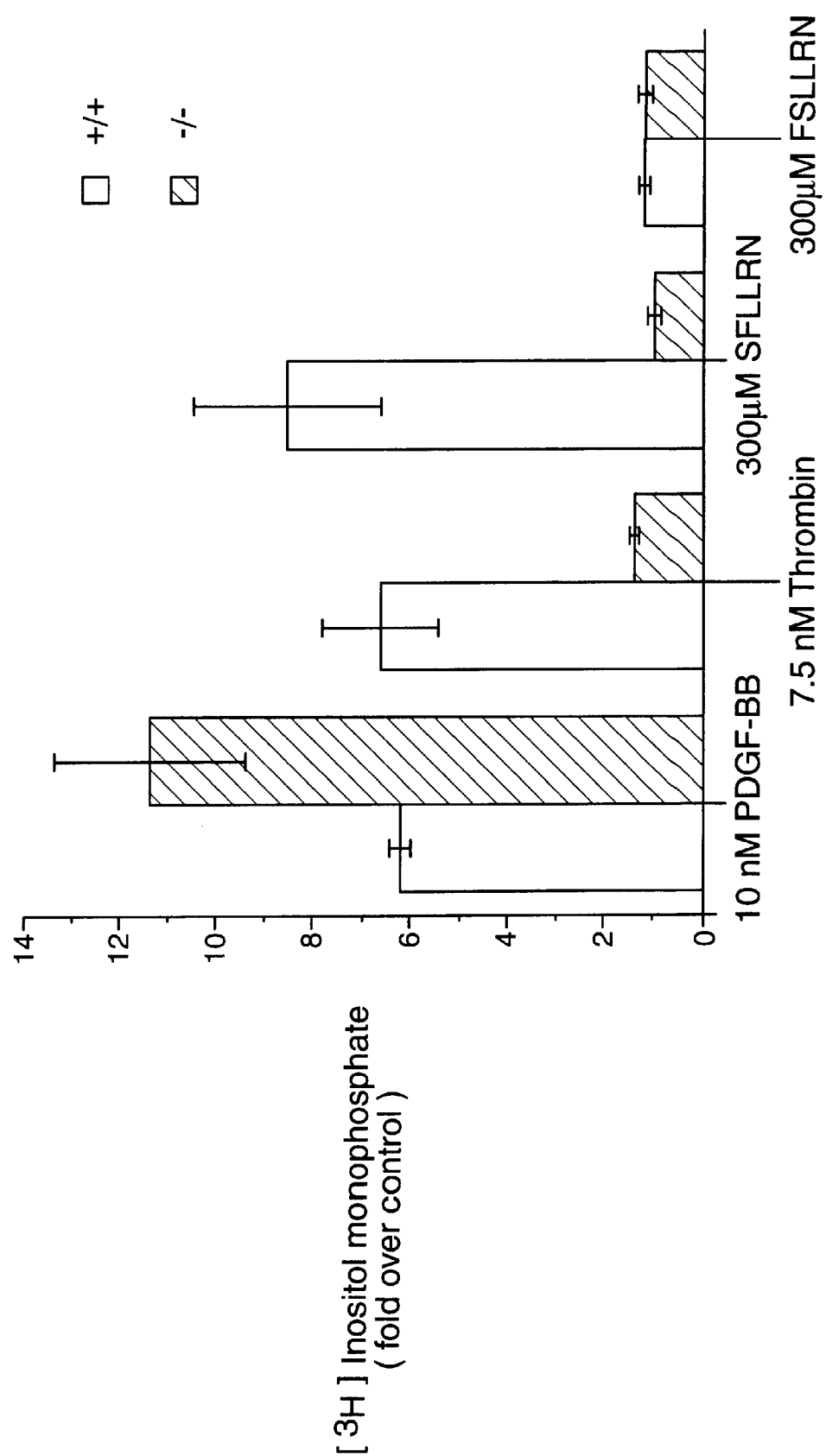
FIG. 6 Thrombin receptor-dependent [$^3$H]inositol monophosphate formation in +/+ and −/− lung cells is shown. Cells were stimulated with human-thrombin (7.5 nM), SFLLRN-NH$_2$ [SEQ.ID.NO.:4] (300 μM), FSLLRN-NH$_2$ [SEQ.ID.NO.:5] (300 μM) as a the negative control, and PDGF-BB (10 nM) as a positive control. Results represent the mean ± standard error from two independent cultures for each group.

A thrombin receptor null mutation was demonstrated by examining thrombin receptor-mediated signal transduction (phosphoinositide hydrolysis) in cultured lung cells (FIG. 6). Lung tissue was removed, minced and digested with 4 mg/ml type I collagenase (Worthington). Cell suspensions were washed twice and seeded in 75 cm$^2$ flasks in DMEM containing 10% heat-inactivated FBS and antibiotics. Non-adherent cells were removed by washing at 24 hours. At 70% con-fluence, cells were trypsinized and plated at 5×10$^4$ cells/well in 12-well cluster dishes. Measurement of [$^3$H] inositol phosphate formation was performed as previously described [R. J. Santulli et al., Proc. Natl. Acad. Sci. USA 92, 9151 (1995)] with the exception that cells were radio-labeled for 24 hours in inositol-free DMEM. Both thrombin and the ThrR-activating peptide SFLLRN-NH$_2$ [SEQ.ID.NO.:4] (sequence corresponding to the receptor amino terminus following thrombin cleavage) stimulated a significant increase in [$^3$H]inositol monophosphate formation in +/+ cells, whereas no response was observed in cells derived from null mice (FIG. 6). The cells derived from ThrR null mice were stimulated by PDGF-BB indicating that they could respond to another mitogenic substance that induces phosphatidylinositol hydrolysis.

Platelet function was examined in ThrR-deficient mice by monitoring whole blood aggregation via ATP release after agonist stimulation [C. Ingerman-Wojenski, B. B. Smith, M.

J. Silver, J. Lab. Clin. Med 101, 44 (1983)]. ATP release was measured in whole blood from +/+, +/− and −/− ThrR mice in response to a-thrombin (0.5, 2, and 5 U/ml), collagen (5,10, and 20 μg/ml) and SFLLRN-NH$_2$ (300 μM) using a whole blood aggregometer (Chronolog Corp., Havertown, Pa.). Blood samples (0.1 ml) were diluted in saline to result in a final 1:2.5 dilution of blood after the additions of other reagents. The diluted blood was pre-warmed to 37° C. for 5 minutes. Calcium chloride (6 μl, 0.02 M) and luciferin (5 μl, Chronolume, Chrono-Log Corp.) were added to each sample 30–60 seconds before addition of thrombin or collagen. Luminescence due to the release of ATP during aggregation was calculated by Aggrolink software supplied by Chronolog Corp. and compared to the luminescence induced by ATP (2 nmol). The change in luminescence was used to calculate the absolute amount of ATP secreted per sample and the rate of ATP release. ATP release was corrected for the number of platelets. No difference in ATP release in response to thrombin or collagen was observed among the +/+, +/−, and −/− ThrR mice. SFLLRN-NH$_2$ [SEQ.ID.NO.:4] failed to induce ATP release in whole blood from +/+, +/−, and −/− mice at concentrations up to 300 μM. These data are consistent with previous observations on platelets from mice (and rats): although responsive to thrombin, such platelets are insensitive to ThrR-activating peptides [T. M. Connolly et al., Thromb. Haemostasis 70, 627 (1994); C. K. Derian, R. J. Santulli K. A. Tomko, B. J. Haertlein, P. Andrade-Gordon, Thromb. Res. 78, 505 (1995)]. In addition, analysis of RNA from rat platelets by using highly sensitive RT/PCR methodology indicated the absence of ThrR mRNA, and suggests the absence of this receptor in wild-type mouse platelets. The response of mouse platelets to thrombin could be attributed to other thrombin-sensitive receptors or by a yet-unidentified mechanism.

Various hematological, coagulation, and hemodynamic parameters of the +/+, +/−, −/− mice were analyzed and the results are shown in Table 2.

TABLE 2

| Parameter | +/+ | +/− | −/− |
| --- | --- | --- | --- |
| WBC (×10³/μl) | 4.3 ± 0.5 | 5.5 ± 1.4 | 4.2 ± 1.2 |
| RBC (×10³/μl) | 7.5 ± 0.2 | 7.8 ± 0.5 | 8.0 ± 0.4 |
| Platelet (×10³/μl) | 768 ± 48 | 902 ± 114 | 926 ± 40 |
| APTT (s) | 10.0 ± 0.1 | 10.3 ± 0.4 | 10.0 ± 0.1 |
| PT (s) | 29.2 ± 1.4 | 27.0 ± 1.3 | 32.0 ± 2.2 |
| Fibrinogen (mg/dl) | 194 ± 15 | 180 ± 20 | 207 ± 3 |
| SAP (mm Hg) | 104 ± 5 | 106 ± 4 | 100 ± 9 |
| DAP (mm Hg) | 79 ± 4 | 80 ± 4 | 81 ± 4 |
| MAP (mm Hg) | 91 ± 4 | 92 ± 4 | 90 ± 6 |
| HR (bpm) | 413 ± 13 | 422 ± 26 | 464 ± 45 |

Data is expressed as mean ± se. Abbreviations are as follows: APTT, activated partial thromboplastin time; PT, prothrombin time; SAP, systolic arterial pressure; DAP, diastolic arterial pressure; MAP, mean arterial pressure; HR, heart rate (bpm=beats/min).

Whole blood cell counts, hemoglobin, and hematocrit values were determined with a hematology analyzer (Sysmex K-1000, Toa Medical Electronics Co., LTD., Kobe, Japan) by using a 100-μl whole blood sample collected in 7.5% potassium EDTA (5:1 v/v). Arterial blood samples were collected in 7.6% sodium citrate (18:1 v/v) for ex vivo assessment of platelet aggregation. Samples for measurement of PT, APTT, and fibrinogen concentration were collected in 7.6% sodium citrate (18:1 v/v). Data were collected on a MCA-110 Microsample Coagulation Analyzer (Bio/data, Hatboro, Pa.). For PT determination, thromboplastin C (50 μl; Instrumentation Laboratory) was added to 25 μl of citrated plasma. The concentration of fibrinogen was determined by a Kinetic Fibrinogen Assay (KFA™, Bio/data) from the change in optical density measured during PT determination. For measurement of APTT, APTT-C (25 μl, Instrumentation Laboratory Company, Lexington, Mass.) was incubated with 25 μl of citrated plasma at 37° C. for 3 minutes followed by addition of CaCl$_2$ (25 μl, 0.20 M) to the incubation mixture. Statistical analyses were performed by ANOVA. Blood counts, APTT, PT, fibrinogen concentrations, basal heart rates, and arterial pressures of the +/+ controls and −/− ThrR mice were not significantly different. Thus, despite the fact that ThrR is normally expressed in multiple cardiovascular tissue types, ThrR deficiency has no detectable impact on these basal cardiovascular characteristics in normal adult mice.

Figures 7C, 7D:
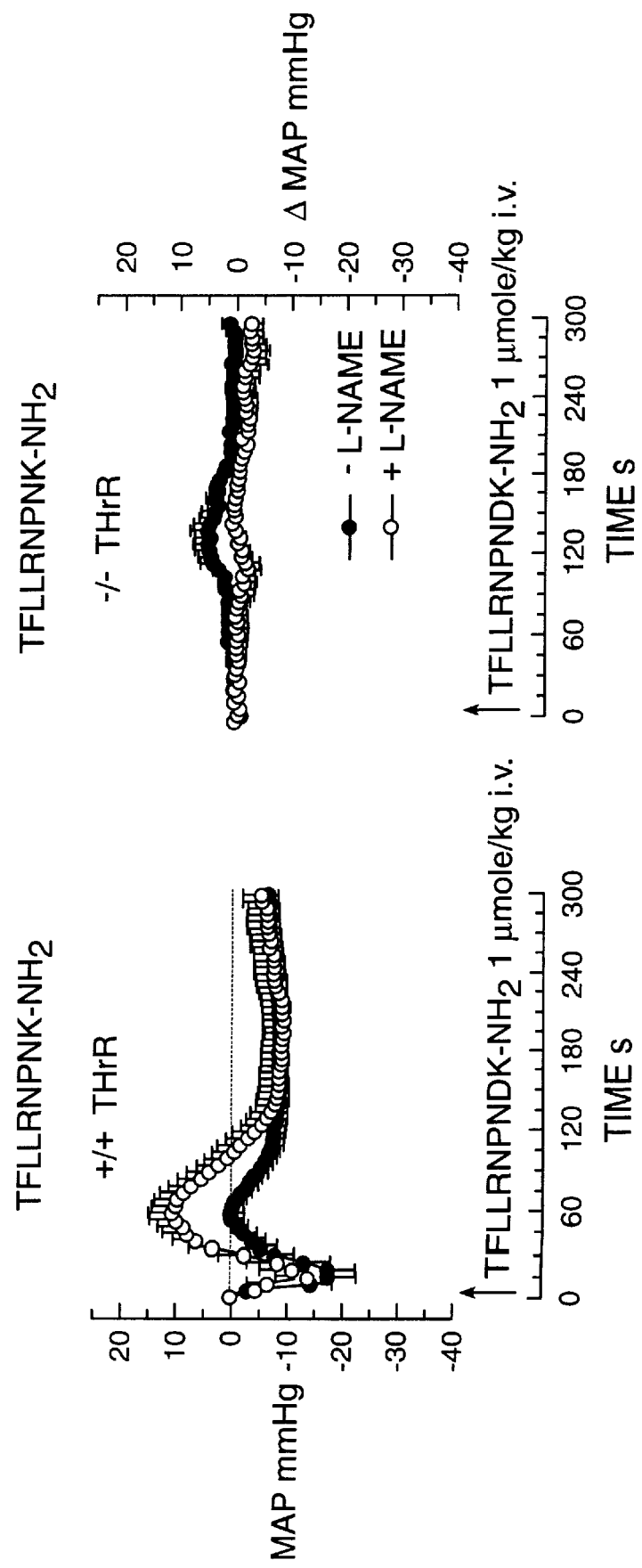
FIG. 7 Panels A and B Effects of SFLLRN-NH$_2$ on mean blood pressure in +/+ and −/− ThrR mice are shown. Filled circles show responses versus time before L-NAME; open circles show responses versus time following L-NAME (30 mg/kg, IV).
Figure 8B:
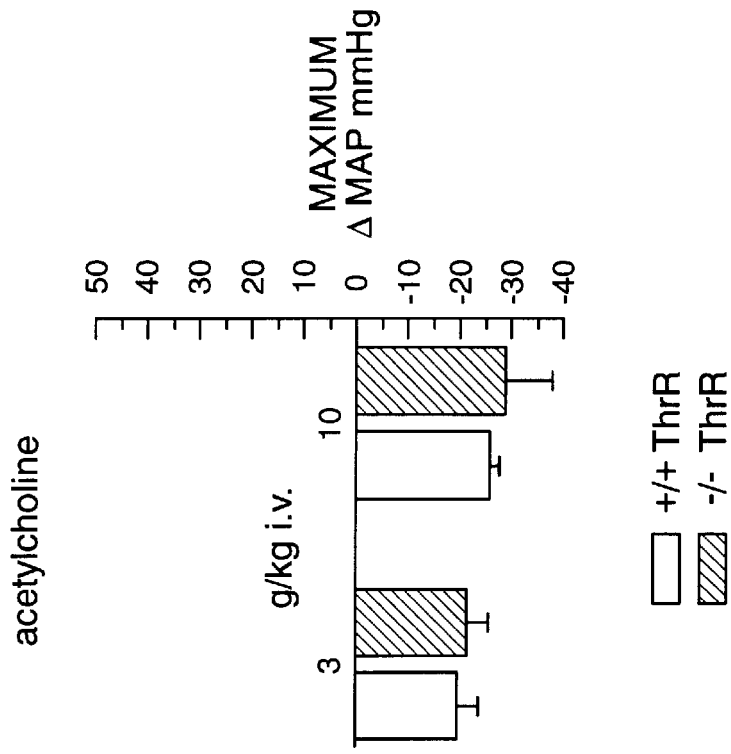
FIG. 8 Panels A and B Maximal blood pressure responses to angiotensin II alone (A) and acetylcholine alone (B) in +/+ and −/− ThrR mice.
Figure 8A:
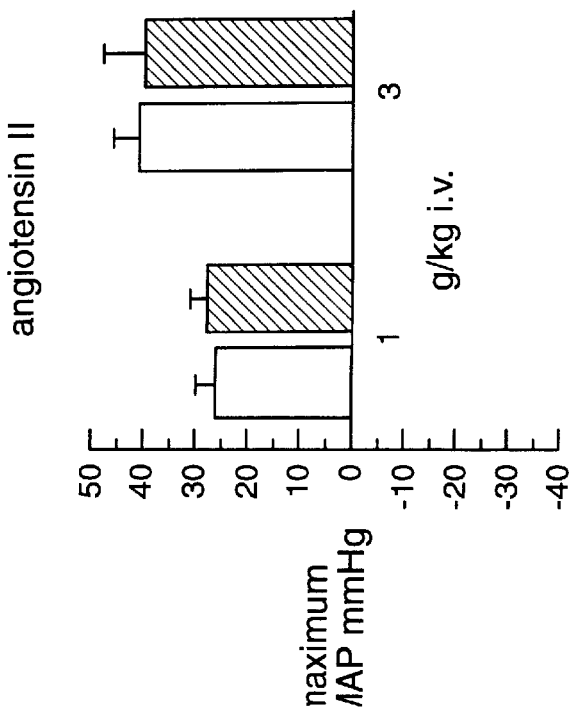

In isolated vascular ring preparations, thrombin alters vascular tone via ThrR on vascular endothelium and smooth muscle cells [R. P. White, C. E. Chapleau, M. Dugdale, J. T. Robertson, Stroke 11, 363 (1980); J. G. De Mey, M. Claeys, P. M. Vanhoutte, J. Pharmacol. Exp. Ther. 222, 166 (1982)]. These vasomotor actions of thrombin are complex, involving both endothelium-dependent relaxation and endothelium-independent contraction, which are mimicked by ThrR-activating peptides [M. J. Antonaccio, D. Normandin, R. Serafino, S. Moreland, J. Pharmacol. Exp. Ther. 266, 125 (1993); B. Tesfamariam, G. T. Allen, D. Normandin, M. J. Antonaccio, Am. J. Physiol. 265, H1744 (1993); D. D. Ku, J. K. Zaleski. J. Cardiovasc. Pharmacol. 22, 609 (1993)]. This characteristic of SFLLRN-NH$_2$ [SEQ.ID.NO.:4] was utilized to verify the loss of ThrR in the vasculature of the −/− mice. Male mice, at least 4 months old and weighing 30–35 g, were anesthetized with isoflurane (1.25%). A medial cervical incision was made, the trachea was cannulated (PE-90); the animals were ventilated with a gas mixture of isoflurane (0.75%), oxygen (95%), and carbon dioxide (5%) at 140 breaths/min and a tidal volume of 0.2 ml, using a rodent respirator. Body temperature was maintained at 38° C. with a heating lamp and a proportional temperature controller. Subdermal needle electrodes were inserted for recording lead II electrocardiogram (ECG). A Teflon AWG30 tubing, tapered at one end, was filled with heparin (10 U/ml) and inserted into the right carotid artery, advanced to the thoracic aorta and attached to a Statham P50 pressure transducer (Spectramed, Oxnard, Calif.) for recording arterial blood pressure. A Mico-Renthane® MRE-033 (Braintree Scientific, Inc., Braintree, Mass.) tubing was inserted into the right jugular vein for administration of drugs. All hemodynamic and ECG measurements were recorded and analyzed with a digital data acquisition system (HD5/16/SW, Po-Ne-Mah, Simsbury, Conn.). Blood pressure and ECG were continuously monitored during the study. Baseline values were recorded for at least 30–60 minutes until stable. Mice were then given a bolus infusion of SFLLRN-NH$_2$ [SEQ.ID.NO.:4] (0.3 mg/kg) and hemodynamic parameters monitored for 10 minutes. Twenty to 30 minutes after SFLLRN-NH$_2$ [SEQ.ID.NO.:4], angiotensin II (1 and 3 μg/kg), or acetylcholine (3 and 10 μg/kg), diluted in saline, were infused with 10 minutes between doses. Twenty minutes after the last infusion, L-NAME (30 mg/kg) was administered as an intravenous bolus infusion. Five minutes after L-NAME administration, responses to SFLLRN-NH$_2$ [SEQ.ID.NO.:4], angiotensin, and acetylcholine were measured. For each genotype at least three mice were analyzed and the results are shown in FIG. 7. In +/+ mice, SFLLRN-NH$_2$ [SEQ.ID.NO.:4] (0.3 mg/kg, i.v.) produced an immediate, transient decrease in mean arterial pressure (MAP) followed by a return to control levels (FIG. 7A). After treatment with L-NAME (N-nitro-L-arginine methyl ester), an inhibitor of nitric oxide synthesis, the MAP increased. When SFLLRN-NH$_2$ [SEQ.ID.NO.:4] was administered following L-NAME, MAP decreased to a similar extent, then increased significantly above control values. In ThrR −/− mice, the hypotensive response to SFLLRN-NH$_2$ before and after L-NAME was comparable to that in +/+ mice (FIG. 7B). However, SFLLRN [SEQ.ID.NO.:4]-induced hypertension in the presence of L-NAME was absent in −/− mice (FIG. 7B). The depressor response to SFLLRN-NH$_2$, which was comparable in both +/+ and −/− mice, may result from a nonspecific vagal reflex and/or activation of the protease activated receptor-2 (PAR-2) [S. Nystedt, K. Emilsson, C. Wahlestedt, J. Sundelin Proc. Natl. Acad. Sci USA. 91, 9208 (1994)]. Elimination of the hypertensive response to SFLLRN-NH$_2$ [SEQ.ID.NO.:4] following L-NAME is consistent with the lack of functional vascular ThrR in −/− mice. The capacity of the peripheral vasculature to respond to the vasoactive substances angiotensin II and acetylcholine was not altered in the absence of ThrR (FIG. 8, A and B). ThrR deficiency does not appear to affect normal vascular tone; however, the role of ThrR on local thrombin generation during vascular injury and thrombosis remains to be determined.

The deficit for thrombin receptor presented here shows surprisingly few phenotypic changes in adult mice. In sharp contrast, there were profound effects of ThrR deficiency on fetal development. It is possible that other cellular mechanisms may compensate for this introduced mutation in the surviving mice, leading to phenotypically normal ThrR −/− adult offspring. The presence of other thrombin-sensitive receptors, as well as additional protease-activated receptors, such as PAR-2, may provide a functional redundancy for ThrR. However, these compensatory effects are not generally expressed during fetal development as seen by the high partial lethality. Our results also indicate that thrombin activation of mouse platelets occurs in the absence of the cloned thrombin receptor. The availability of ThrR −/− mice represents a valuable tool for determining the involvement of ThrR in the pathogenesis of disease and for discovering potential new modes of therapy.

EXAMPLE 7

Evaluation of the Rate and Quality of Healing in Full-Thickness Excisional Wounds in Thrombin Receptor −/− Mice Experimental Procedure: Wild type mice (n=1) and thrombin receptor −/− mice (n=10) were anesthetized and one full-thickness excisional wound (1.0 cm$^2$) was made on the dorsal region approximately 1 cm to the right of the spine and 2.5 cm from the base of the skull. Wounds were visually assessed for qualitative and quantitative measures of healing including dressing conditions, wound bed conditions, and wound contraction (captured by digital imaging techniques) on days 2, 5, 7, 9, and 14 post-wounding. Histological assessment and quantitative immunohistochemical analyses were performed on tissue samples obtained on day 14.

Results: The contraction rate of full-thickness excisions was significantly decreased in thrombin receptor -l- mice as compared to wild-type mice after 7, 9 and 14 days post-wounding (FIG. 9). Immunolabeling intensity for factor VIII-related antigen (angiogenic marker), smooth muscle actin (marker for myofibroblast phenotype), proliferating cell nuclear antigen and leukocyte common antigen (inflammatory marker) were lower in the thrombin receptor -l- mice in comparison to wild-type mice at 14 days post-wounding.

Conclusions: These results show that the thrombin receptor contributes to processes involved in the response to injury including the inflammatory, angiogenic, and contractile responses. The thrombin receptor −/− mice are a useful model for assessment of wound healing, including the discovery and development of compounds to modulate wound healing.

---

---

What is claimed is:

1. A transgenic mouse comprising a homozygous disruption of a gene encoding α-thrombin receptor in its somatic and germ cells wherein said disruption results in an inability of said mouse to produce detectable levels of α-thrombin receptor and further wherein said mouse has a significantly decreased contraction rate of full-thickness excisions and an increased incidence of embryonic lethality as compared to a non-transgenic mouse.

2. The mouse of claim 1, wherein said mouse is fertile and transmits the disrupted a-thrombin receptor gene to its offspring.

3. The mouse of claim 1 wherein the disrupted α-thrombin receptor gene has been introduced into an ancestor of the mouse at an embryonic stage by microinjection of embryonic stem cells into mouse blastocysts, wherein the embryonic stem cells comprise a disrupted α-thrombin receptor gene.

4. A method of producing a mouse using embryonic stem cells, wherein the somatic and germ cells of said mouse contain a disrupted α-thrombin receptor gene, which comprises:

(a) introducing a gene construct that disrupts the α-thrombin receptor gene in mouse embryonic stem cells;

(b) injecting the embryonic stem cells containing the disrupted α-thrombin receptor gene into mouse blastocysts;

(c) implanting the resultant chimeric blastocyst into a pseudopregnant mouse.

(d) allowing the embryo to develop producing a chimeric mouse comprising a disrupted α-thrombin receptor gene in its germ line;

(e) breeding said chimeric mouse to generate a heterozygous mouse comprising a disrupted α-thrombin receptor gene;

(f) interbreeding said heterozygous mice and selecting progeny that are homozygous for said disrupted α-thrombin receptor gene.

5. The method of claim 4 wherein the introducing of step (a) is by electroporation, and the injecting in step (b) is by microinjection.

6. An isolated cell line derived from the transgenic mouse of claim 1.

* * * * *